United States Patent [19]

Seidel et al.

[11] 4,271,308
[45] Jun. 2, 1981

[54] 4-ALKYL-1,2,4-4H-TRIAZOLE DERIVATIVES

[75] Inventors: Michael C. Seidel, Chalfont, Pa.; William C. von Meyer, Charlotte, N.C.; Stanley A. Greenfield, Ambler, Pa.

[73] Assignee: Rohm and Haas Company, Philadelphia, Pa.

[21] Appl. No.: 48,426

[22] Filed: Jun. 14, 1979

Related U.S. Application Data

[60] Division of Ser. No. 924,467, Jul. 14, 1978, which is a continuation-in-part of Ser. No. 267,766, Jun. 30, 1972, Pat. No. 4,120,864, which is a continuation-in-part of Ser. No. 67,198, Aug. 26, 1970, abandoned, which is a continuation-in-part of Ser. No. 847,481, Jul. 3, 1969, Pat. No. 3,701,784, which is a continuation-in-part of Ser. No. 757,490, Sep. 4, 1968, Pat. No. 3,769,411.

[51] Int. Cl.$^3$ ............... A01N 43/64; C07D 249/08
[52] U.S. Cl. ............................... 548/262; 424/269
[58] Field of Search ................. 260/308 R; 548/262

[56] References Cited

PUBLICATIONS

Greenfield et al., Chem. Abstracts, vol. 72, abstract No. 100713(q) (1970).
Ainsworth et al., J. Med. Chem., vol. 5, pp. 383–389 (1962).

*Primary Examiner*—Alton D. Rollins
*Attorney, Agent, or Firm*—Bernard J. Burns; Alex R. Sluzas

[57] ABSTRACT

Substituted 1,2,4-4H-triazoles of the formula

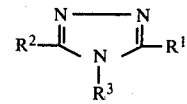

wherein $R^1$ and $R^2$ are hydrogen atoms and
$R^3$ is alkyl, alkenyl, alkynyl, cycloalkyl benzyl or phenyl. These compounds are fungicides and are particularly useful for the control of cereal rust.

6 Claims, No Drawings

4-ALKYL-1,2,4-4H-TRIAZOLE DERIVATIVES

This is a division of application Ser. No. 924,467 filed July 14, 1978, which was a continuation-in-part of U.S. Ser. No. 267,766 filed June 30, 1972, now U.S. Pat. No. 4,120,864 which in turn is a continuation-in-part of U.S. Ser. No. 67,198 filed Aug. 26, 1970, abandoned which in turn is a continuation-in-part of U.S. Ser. No. 847,481, filed July 3, 1969, U.S. Pat. No. 3,701,784, which in turn is a continuation-in-part of Ser. No. 757,490, filed Sept. 4, 1968, U.S. Pat. No. 3,769,411.

This invention is concerned with substituted 1,2,4-4H-triazoles, hereinafter termed 1,2,4-triazoles, which possess fungicidal properties useful for the control of fungal diseases on plants and in some instances herbicidal properties and to agricultural compositions containing them. It also relates to certain of these 1,2,4-triazoles which are useful as systemic fungicides for the control of a rust disease, as on a cereal crop.

The chemistry of the 1,2,4-triazoles has been reviewed by K. T. Potts in Chemical Reviews 61, 87–127 (1961). A few such compounds are known to possess biological properties. 3-Amino-1,2,4-triazole is a commercial herbicide, and thiocarbamyl derivatives of it possess fungicidal properties useful for paints according to French Pat. No. 1,425,253. Japanese Pat. Publ. 11480/66 discloses certain 3-mercapto-4-amino-5-(substituted-methyl)-1,2,4-4H-triazoles as fungicides. 5-Amino-1-bis(dimethylamino)-phosphenyl -3-phenyl-1,2,4-triazole is a known fungicide. U.S. Pat. No. 3,308,131 discloses among others 3-mercapto-1-(substituted-carbamyl)-1,2,4-triazoles useful as insecticides.

Relatively few compounds are known to control fungal rust organisms and still fewer which control them by systemic action. Rust fungicides include symmetrical-dichlorotetrafluoroacetone, ethylenebisdithiocarbamates, nickel compounds, phenyl-hydrazones, cycloheximide and certain carboxamido oxathiins.

The substituted 1,2,4-triazoles of this invention which have been found useful as fungicides for the control of phytopathogenic fungi are represented by the general formula

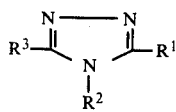
(I)

wherein $R^1$ is hydrogen or —SA wherein A is (a) hydrogen, (b) alkyl groups of 1 to 12 carbon atoms and alkyl groups of 1 to 12 carbon atoms substituted by (1) halogen, preferably chlorine, (2) lower alkoxy (3) cyano, (4) carbamyl, (5) alkenyloxy of 3 to 6 carbon atoms, (6) phenoxy, (7) phenyl, (8) lower alkoxy, lower alkyl, halo preferably chloro or nitro substituted phenyl, (9) benzoyl and (10) halo preferably chloro, lower alkoxy, lower alkyl or nitro substituted benzoyl, (c) alkenyl of 3 to 6 carbon atoms, (d) the group —C(X)$R^4$ wherein X is O or S and $R^4$ is selected from the group consisting of lower alkyl, methoxy substituted lower alkyl, phenyl, lower alkyl substituted phenyl, lower alkoxy substituted phenyl, halo and nitro substituted phenyl, furyl and the group —NR$^5$R$^6$ wherein $R^5$ and $R^6$ may be hydrogen or lower alkyl groups, (e) the group —CH(OH)$R^7$ wherein $R^7$ is hydrogen, lower alkyl or lower halo-substituted alkyl, (f) the group

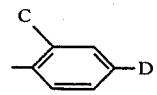

wherein C and D are hydrogen and a meta-directing group such as cyano, nitro, sulfonic acid and sulfonic acid derivatives with the proviso that only one of C and D may be hydrogen, (g) salt-forming metals such as the alkali and alkaline earth metals, cadmium, copper, iron, manganese, nickel, tin and zinc;

$R^2$ is (a) alkyl, straight or branched, of 1–18 carbon atoms which may be substituted with hydroxy, lower alkoxy, lower-alkylamino, di(lower alkyl) amino, phenyl, methoxy-substituted phenyl, phenoxy or thiophenoxy which may be substituted in the phenyl group with halo preferably chloro, lower alkyl, lower alkoxy or nitro, an imidazolyl group, a 1,2,4-triazyl group, or a COY group wherein Y is hydroxy or lower alkoxy, (b) alkenyl of 3 to 6 carbon atoms, (c) alkynyl of 3 to 6 carbon atoms, (d) cycloalkyl of 3 to 8 carbon atoms, (e) benzyl which may be substituted in the phenyl group with lower alkyl, halo preferably chloro and nitro groups, (f) phenyl which may be substituted with halo preferably chloro, lower alkyl, lower alkoxy, cyano or nitro groups, or (g) heterocyclic group selected from the group consisting of 2-pyridyl, 4-pyridyl, 2-pyrimidyl, 3-(and 4-)-1,2,4-triazyl, 1-morpholinyl, 2-thiazyl 2-benzothiazyl, 2-benzimidazolyl and their halo preferably chloro substituted derivatives; and $R^3$ is hydrogen, lower alkyl, hydroxy, furyl, and the group —COOB wherein B is hydrogen, lower alkyl, ammonium, ammonium monosubstituted with lower alkyl or lower hydroxyalkyl ammonium disubstituted with lower alkyl or lower hydroxyalkyl, ammonium trisubstituted with lower alkyl or lower hydroxyalkyl, quaternary ammonium and salt-forming metals; and acid salts of the basic substituted 1,2,4-triazoles prepared from mineral acid such fluoboric, hydrobromic, hydrochloric, nitric, phosphoric and sulfuric and from mono and polybasic organic acids such as acetic, chloroacetic, acrylic, toluene-sulfonic, oxalic and maleic.

When the term "lower" is employed in conjunction with alkyl and alkoxy as above it is intended to indicate that the alkyl or alkyl portion thereof has a carbon content of 1 to 5 carbon atoms. Alkyl groups as referred to for Formula I may be straight or branched chain.

Compounds of Formula I in which $R^1$ is SH may exist in tautomeric form; thus,

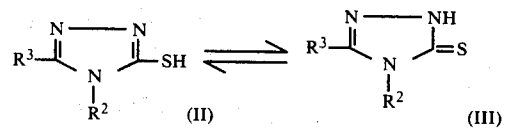

Formula II is a 1,2,4-4H-triazole whereas Formula III is more properly known as a Δ²-1,2,4-triazoline-5-thione. Compounds derived from such a tautomeric mixture by introduction of an A group, as defined above except possibly for metallic salts, could therefore exist as

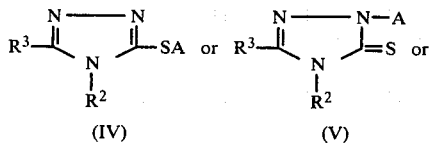

(IV)     (V)

as mixtures of these. However, for the present purpose these compounds will be referred to as 1,2,4-4H-triazoles or more simply as 1,2,4-triazoles.

Further when $R^3$ is OH two additional tautomers are possible, thus,

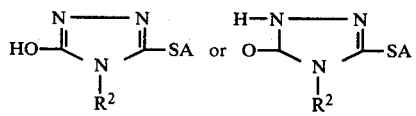

It is quite probable that the major component is in the lactam form; however, for the present purpose the 5-hydroxy-1,2,4-triazole form will be used. For a general discussion of tautomeric compounds and of the isomers that may result from synthetic procedures for producing triazoles reference is made to Elderfield, "Heterocyclic Compounds", John Wiley, N. Y., 1957, Vol. V, pp. 91–92.

Various methods are available for the preparation of the compounds of Formula I.

A. For the compounds where $R^1$ and $R^3$ are hydrogen,

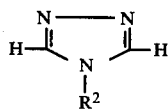 (VI)

The method of Bartlett and Humphrey, J. Chem. Soc. 1967, 1664–1666, involving a transamination of N,N-dimethylformamide azine may be used; thus

The reaction usually involves heating to remove the dimethylamine and may be run in the presence of a solvent such as an aromatic hydrocarbon. An acidic catalyst may be used.

The method of Pellizzari (Chemical Reviews 61, 95 (1961) involves diformhydrazide with primary amines; thus

The method of U.S. patent 3,647,814 which involves reaction of a primary amine with an N-alkoxymethylene-N'-formylhydrazine.

B. For the compounds where $R^1$ is SH and $R^3$ is hydrogen,

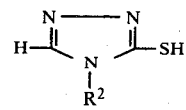 (VII).

This involves reaction of hydrazine with an isothiocyanate ($R^2NCS$) to produce a semicarbazide which is then formylated followed by cyclization in the presence of a base catalyst; thus

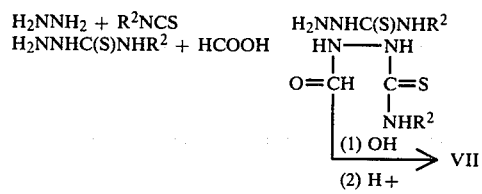

This general method is described in Organic Syntheses 40, 99 (1960) and Kroger, Sattler and Beyer, Annalen 643, 128 (1961). The formation of the semi-carbazide and its formylation are standard type reactions, e.g. see Lieber, Pillai and Hites, Canadian Journal of Chemistry 35, 832 (1957). These intermediates may, if desired be isolated prior to the cyclization reaction. The cyclization reaction may be conveniently carried out in the presence of a base catalyst. Cyclization may be optimized by the use of from 2 to 3 equivalents of the base catalyst. The cyclization catalyst can be selected from inorganic base catalysts such as metal hydroxides, carbonates and bicarbonates, or organic base catalyst such as triethylamine, pyridine and N,N-dimethyl-aniline. Sodium hydroxide is a readily available base catalyst for use in the cyclization reaction.

Since the intermediate products prior to cyclization are usually solids, a reaction solvent is usually necessary. The cyclization reaction may be conveniently carried out in any solvent medium that is inert under the reaction conditions. Suitable solvents are water, alcohols such as methanol, butanol and propanol, benzene, hexane, or other suitable inert organic solvents such as dimethylformamide, ether, dimethylsulfoxide, etc.

The cyclization reaction temperature is not critical. Temperatures in the range of −10° C. to 100° C. may be used, with temperatures in the range of 25° to 75° C. being preferred.

An alternate procedure for producing compounds of Formula VII is to react the intermediate semicarbazide with ethyl formate in the presence of an alkali alkoxide, such as sodium methoxide, and heating the mixture to produce the 1,2,4-triazole; thus

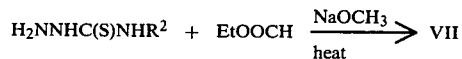

The general method is described by Pesson, Polmanss and Dupin Compt. rend. 248, 1677 (1959).

The removal of the mercapto group in a 1,2,4-triazole by oxidation, such as with nitric acid, or hydrogen peroxide is known from the work of Wohl and Marchwald, Berichte 22, 576 (1889). Thus compounds of Formula IV may be produced from those of Formula VII.

C. For the compounds where $R^1$ is SH and $R^3$ is a group other than hydrogen or carboxyl,

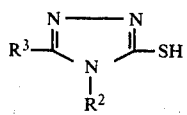 (VIII)

The cyclization of a 1-acyl-4-substituted thiosemicarbazide by an alkaline substance or by heat has been studied as an efficient route to compounds of Formula VIII (Chemical Reviews 61, 99 (1961)); thus

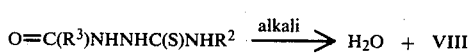

An alternate procedure involves the reaction of a 4-substituted thiosemicarbazide with an acid ester, e.g. the ethyl ester, in the presence of a sodium alkoxide, e.g. sodium ethoxide; thus

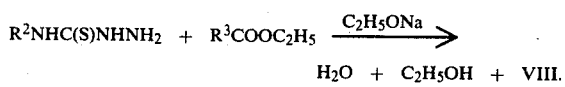

When in the above reaction the acid ester is a carbonate, such as ethyl carbonate, the resulting compound contains an OH group as the $R^3$ substituent,

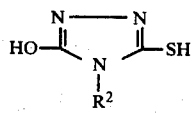 (IX)

Compounds of Formula IX have been prepared by cyclizing 1-substituted-2-thiobiureas as described by Bradsher et al. in the Journal of Organic Chemistry 23, 618 (1958).

D. For the compounds where $R^1$ is SH and $R^3$ is COOH,

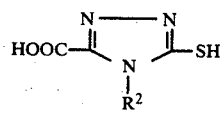 (X)

This method involves reaction of a dialkyl oxalate such as diethyl oxalate with hydazine to produce an alkyloxalyl hydrazide, which is then reacted with an isothiocyanate ($R^2NCS$) produce a semicarbazide, followed by cyclization in the presence of a base catalyst such as sodium alkoxide or triethylamine. This produces the carboxylic ester of the Formula X compound, which upon acid hydrolysis gives the free acid. This may be illustrated with diethyl oxalate, thus

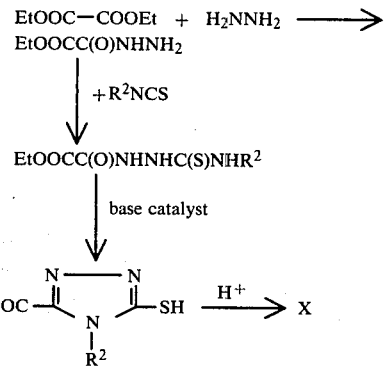

In this reaction it has been found that the formation of the alkyloxalyl hydrazide intermediate is enhanced by conducting the reaction at reduced temperatures, e.g. $-10°$ C. to $10°$ C. Further, reaction and storage temperature conditions are more important with regard to the stability of the 1,2,4-triazoles having a carboxy group in the 5-position, i.e. when $R^3$ is COOH. These compounds are readily decarboxylated when held at $130°$ C. for about 30 minutes or at about $45°$ C. for about 4 hours. An acid catalyst often produces decarboxylation under milder conditions. Thus, decarboxylation of compounds of Formula X is another way of preparing compounds of Formula VII.

E. Compounds of the type

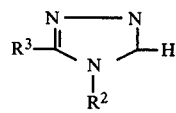 (XI)

may be prepared by removal of the mercapto group of compounds of Formula VIII and IX by reaction with oxidizing agents such as nitric acid or hydrogen peroxide. F. Salts of various of the substituted 1,2,4-triazoles may be made by methods known to one skilled in the art. Thus, (1) The basic 1,2,4-triazoles may be reacted with mineral and organic acids, e.g. see Ainsworth et al. J. Med. Pharm. Chem. 5, 383 (1962).

(2) those compounds where $R^1$ is SH group may be reacted with bases such as alkali and alkaline earth hyroxides, oxide and carbonates. Of the alkali salts the sodium salt is preferred. The relatively insoluble heavy metal salts may be made by reacting a water-soluble salt of the heavy metal with a water-soluble salt of the 1,2,4 triazole.

(3) those compounds where $R^3$ is carboxy may be reacted with metallic bases such as alkali and alkaline earth hydroxides, oxides and carbonates; ammonia and quarternary ammonium hydroxide; and amines. For some salts such as quarternary ammonium and heavy metal ones it is convenient to react a water-soluble quaternary ammonium or metal salt with a water-soluble salt of the 1,2,4-triazole.

G. Derivatives of the 1,2,4-triazoles containing a 3-mercapto group, i.e. where $R^1$ in Formula I is SA, may be made by methods known to one skilled in the art. Thus:

(1) where A is alkyl, alkyl substituted with various groups such as alkoxy and phenoxy; benzyl and substituted benzyl; the group —CH₂C(O)NR⁵R⁶ and the

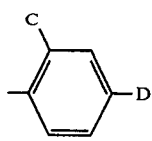

group as defined above, the compounds may be made by reaction of the respective halides with a salt of the 3-mercapto-1,2,4-triazole.

(2) where A is an acyl group such as a benzoyl, furoyl group, carbamoyl or thiocarbamoyl, the acyl halides may be reacted with a salt of the 3-mercapto-1,2,4-triazole.

(3) where A is a lower cyanoalkyl group, the mercapto group of the 1,2,4-triazole of compounds of Formula I, VII and VIII may be reacted with an olefinic nitrile such as acrylonitrile or methacrylonitrile. In some instances compounds of Formula V are known to result and this is particularly true for compounds which give a Michael type addition such as acrylonitrile, methacrylonitrile, acrylic acid, maleic acid, nitroethylene and nitrostyrene A cyano group can also be introduced by other means known in the art such as replacement of a halo atom by reaction with a cyanide salt or by dehydration of a carbamoyl group.

(4) where A is a —C(O)NHR⁵ or —C(S)NHR⁵ group the mercapto 1,2,4-triazoles may be reacted with an isocyanate (R⁵NCO) or isothiocyanate (R⁵NCS).

Details of preparing the compounds of this invention are given in the following examples which are presented for purposes of illustration and are not intended to limit the scope of the invention. Table I lists by structure and name, compounds prepared by the above-described processes and constitutes Examples 1 through 130. Table II gives physical characteristics and analyses or literature references for these examples. Specific illustrative preparations of Examples 1, 69, 76, 83, 88, 90, 94, 102, 106, 110, 112, 114, 124 and 125 are set forth below.

Example 1

Preparation of 4-n-propyl-1,2,4-triazole

A reaction mixture consisting of 10 g. (0.0705 mole) of N,N-dimethylformamide azine, 41.5 g. (0.705 mole) of n-propylamine 0.6 g. of p-toluenesulfonic acid and 200 ml. of benzene was refluxed 4 hrs. and then stripped of solvent. The residue was distilled to give 3.3 g. distilling at 120°–125° C. which was 4-n-propyl-1,2,4-triazole.

Example 69

Preparation of 4-(2-benzothiazyl)-1,2,4-triazole

A reaction mixture consisting of 10 g. (0.0705 mole) of N,N-dimethylformamide azine, 10.6 g. (0.0705 mole) of 2-aminobenzothiazole, 0.6 g. of p-toluenesulfonic acid and 200 ml. of dimethyl formamide was refluxed 16 hrs., then stripped of solvent. The residue was recrystallized twice from ethanol to give 2.5 g. of solid melting at 199°–201° C. This was 4-(2-benzothiazyl)-1,2,4-triazole.

Example 76

Preparation of 3-mercapto-4-n-butyl-1,2,4-triazole.

4-n-Butylthiosemicarbazide (20.0 g. or 0.136 mole) was heated to reflux with a solution of methanol (100 ml.), sodium methoxide (7.55 g. or 0.140 mole) and ethyl formate (20.7 g. or 0.280 mole). After 8 and 16 hours, 10 ml. and 5 ml. of ethyl formate was added to the refluxing solution. After 24 hours total reflux, the solvent was removed under reduced pressure and the residue was dissolved in water (100 ml.). The pH of the solution was adjusted to about 12 with 50% sodium hydroxide solution. This solution was then heated on a steam bath for 45 minutes, cooled and acidified with dilute hydrochloric acid. The resulting oil was extracted into ether. The ether was dried over sodium sulphate and removed under vacuum. The resulting oil was crystallized from ether-hexane to give 11.8 g. (55% yield) of 3-mercapto-4-n-butyl 1,2,4-triazole, m.p. 67°–69° C. The structure was confirmed by its nuclear magnetic resonance spectrum and its mass spectrum.

EXAMPLE 83

Preparation of 3-mercapto-4-cyclohexyl-1,2,4-triazole

Formic acid (90%, 100 ml.) was heated on a steam bath for 15 minutes and then 4-cyclohexylthiosemicarbazide (30 g. or 0.174 mole) was added portionwise. The resulting clear solution was then heated for an additional 60 minutes, diluted with water (50 ml.) and allowed to cool at 0° C. A precipitate was formed. The precipitate (13 g. or 0.065 mole) was collected and added to a solution of sodium hydroxide (2.6 g. or 0.065 mole) in water (25 ml.) and heated on a steam bath for 60 minutes. The solution was cooled and acidified to pH 2 with dilute hydrochloric acid. The precipitate was collected and recrystallized from ethanol to give 5.3 g. of solid m.p. 162°–165° C. The mother liquors from the crystallization were concentrated to give an additional 4.3 g., m.p. 162°–165° C. The total yield was 9.3 g. (78%) of 3-mercapto-4-cyclohexyl-1,2,4-triazole. The structure was confirmed by its nuclear magnetic resonance spectrum and its mass spectrum.

EXAMPLE 88

Preparation of 3-mercapto-4-phenyl-5-hydroxy-2,4-triazole

To a solution of 65 g. (0.48 mole) of phenyl isothiocyanate in 350 cc of ether was added 50 g. (0.48 mole) of ethyl carbazate with stirring. The resulting mixture was heated on a steam bath for 0.5 hr. The precipitate was filtered off and recrystallized from ethanol:water (1:1) to give white crystals melting at 145°–146° C. Forty grams of this solid was heated with 240 cc. of 10% KOH on a steam bath for 30 min. The reaction mixture was cooled and acidified with 50% hydrochloric acid to give 25 g. of crude, air dried solid. This was recrystallized from acetone to give 18 g. of solid melting at 135°–136° C. It is 3-mercato-4-phenyl-5-hydroxy-1,2,4-triazole, or a tautomer thereof, containing one-half molecule of water of hydration.

EXAMPLE 90

Preparation of
3-mercapto-4-methyl-5-(2-furyl)-1,2,4-triazole (A) Preparation of 1-(2-furoyl)-4-methyl thiosemicarbazide Furoyl chloride (31 g. or 0.238 mole) was added dropwise to a slurry of 4-methylthiosemicarbazide (25 g. or 0.238 moles) in dry pyridine (200 ml. cooled to −10°. The slurry was allowed to come to ambient temperature and stirred overnight. The reaction mixture was poured into 1500 ml. of crushed ice, the precipitate was collected, dried and recrystallized from EtOH to give (1-(2-furoyl)-4-methyl thiosemicarbazide (28.0 g.). This melted at 204°–206° C. (doc.) and was found to contain by analysis 42.4% C, 4.6% H, 21.2%, N, 16.1%, O, 15.9% S; $C_7H_9X_3O_2S$ requires 42.2% C, 4.5% H, 21.1% N, 16.1% O, 16.1% S. The structure was confirmed by its infrared spectrum and nuclear magnetic resonance spectrum.

(B) Conversion of 1-(2-furoyl)-4-methyl thiosemicarbazide into 3-mercapto-4-methyl-5-(2-furoyl)-1,2,4-triazole The above thiosemicarbazide (28 g. or 0.141 moles) in methanol (300 ml.) was refluxed overnight in the presence of sodium methoxide (15.2 g. or 0.282 moles). The solvent was then removed under vacuum and the residue was diluted with water (150 ml.). The solution was then acidified with hydrochloric acid, the precipitate was collected, washed with water and dried. The solid was recrystallized from ethanol to give 3-mercapto-4-methyl -5-(2-furyl)-1,2,4-triazole melting at 192°–194° C. The structure was confirmed by its infra-red spectrum and nuclear magnetic resonance spectrum.

EXAMPLE 94

Preparation of
3-mercapto-4-n-butyl-5-carboxy-1,2,4-triazole (A) Preparation of 1-ethyl oxalyl-4-n-butylthiosemicarbazide To a methanolic solution (200 ml.) of diethyl oxalate (100 g. or 0.683 mole) was added a methanolic solution (200 ml.) of hydrazine hydrate (22.9 g. or 0.68 mole). The addition occurred over a two hour period during which period the reaction temperature was maintained at about −5° C. When the addition was completed n-butyl isothiocyanate (78.4 g. or 0.68 mole) was added at −5° C. The cloudy solution was stirred at ambient temperatures for 18 hours. The reaction mixture was filtered, evaporated under reduced pressures to one-half the original volume, and diluted with water (700 ml.). The resulting precipitate was filtered and air dried to give 154.4 g. (92% yield) of 1-ethyloxalyl-4-n-butylthiosemicarbazide, m.p. 127°–28° C. It was found to contain by analysis 38.76% C, 6.23% H, 19.27% N and 14.83% S; calculated for $C_7H_{11}N_3O_2S\cdot H_2O$ is 38.33% C, 5.98% H, 19.16% N and 14.63% S.

(B) Conversion of 1-ethyl oxalyl-4-n-butylthiosemicarbazide into 3-mercapto-4-n-butyl-5-carboxy-1,2,4-triazole The thiosemicarbazide (125.0 g. or 0.507 mole) formed above was added to a solution of sodium hydroxide (45.0 g. or 1.125 moles) in water (500 ml). After 16 hours at ambient temperature, the solution was warmed to 60° C. and cooled. Dilute (37%) hydrochloric acid (112.0 g. or 1.135 moles) was then added cautiously to avoid foaming. The resulting precipitate was filtered and dried at 45° C. in a vacuum oven to give the crude acid (96.5 g., 86% yield), m.p. 120°–122° C. The acid was recrystallized from water (800 ml.) and dried to give essentially pure 3-mercapto-4-n-butyl-5-carboxy-1,2,4-triazole (67.4 g., 61% yield), m.p. 108°–110° C. The structure was confirmed by its nuclear magnetic resonance spectrum and infrared spectrum.

EXAMPLE 102

Preparation of
3-methylmercapto-4-n-butyl-1,2,4-triazole

Iodomethane (9.05 g. or 0.0637 mole) was added to a solution of 10 g. of 3-mercapto-4-n-butyl-1,2,4-triazole, methanol (100 ml.), and sodium hydroxide (2.55 g. or 0.0637 mole). This solution was then refluxed for 2 hours. The solvent was then removed in vacuum and the residue was dissolved in benzene. This solution was washed with water, dried and the benzene removed in vacuum. The residual oil was distilled to give 3-methylmercapto-4-n-butyl-1,2,4-triazole, b.p. 128°–131° C./2 mm. The structure was confirmed by its nuclear magnetic resonance spectrum.

EXAMPLE 106

Cyanoethylation of 3-mercapto-4-n-butyl-1,2,4-triazole

Acrylonitrile (12 g. or 0.224 mole) was added dropwise to a dioxane (30 ml.) solution of 3-mercapto-4-n-butyl-1,2,4-triazole (10 g. or 0.0638 mole) in the presence of a 40% aqueous solution of benzyltrimethylammonium hydroxide (1 ml.). The dark red solution was left standing overnight, and the solvent was removed in vacuum. The tarry residue was taken up in ether, washed with water, dried, and evaporated to dryness. The resulting oil was distilled to give an oil distilling at 168°–175° C./2 mm. Ultraviolet spectra and the teachings of Postoviskii and Shegal, Chemical Abstracts 63, 13242, 1965 indicate this to be 2-(2-cyanoethyl)-4-n-butyl-1,2,4-triazoline-3-thione.

EXAMPLE 110

Preparation of
3-(1-hydroxy-2,2,2-trichloroethylmercapto)-4-n-butyl-1,2,4-triazole 3-Mercapto-4-n-butyl-1,2,4-triazole (2.0 g. or 0.127 mole) and chloral (3.68 g. or 0.0254 mole) were heated in benzene (30 ml.) until a precipitate formed (10 minutes). The mixture was cooled, the precipitate was collected, dried, and recrystallized from ether-hexane to give 3-(1-hydroxy-2,2,2-trichloroethylmercapto)-4-n-butyl-1,2,4-triazole melting at 95°–97° C. The structure was confirmed by its nuclear magnetic resonance spectrum.

EXAMPLE 112

Preparation of
3-(4-methoxybenzylmercapto)-4-n-butyl-1,2,4-triazole

To a mixture of 10 g. (0.064 mole) of 3-mercapto-4-n-butyl-1,2,4-triazole and 2.6 g. (0.064 mole) of sodium hydroxide in 200 ml. of methanol was added 9.9 g. (0.064 mole) of p-methoxybenzyl chloride. The reaction mixture was heated at reflux about 20 hours. The solvent was evaporated off, the residue washed with water, dried and distilled. There was obtained 17.8 g. of yellow liquid distilling at 190°–205° C. at 0.03 mm. Nuclear magnetic resonance and ultraviolet spectra indicated this to be approximately an equal mixture of 3-(4-methoxybenzylmercapto)-4-n-butyl-1,2,4-triazole and 4-n-butyl-2-(4-methoxybenzyl)-1,2,4-triazoline-3-thione.

EXAMPLE 114

Preparation of 3-methylcarbamoylmercapto-4-n-butyl-1,2,4-triazole

To 6.0 g. (0.0382 mole) of 3-mercapto-4-n-butyl-1,2,4-triazole dissolved in 50 ml. of ether was added 2.5 g. (0.248 mole) of triethylamine and then 2.5 g. (0.0438 mole) of methyl isocyanate. The resulting orange-brown solution was allowed to stand overnight. The solid which formed was filtered and washed twice with 50 ml. of ether to give 4.7 g. (57% yield) of 3-methylcarbamoylmercapto-4-n-butyl-1,2,4-triazole melting at 112°–114° C.

EXAMPLE 124

Preparation of 3-furoylmercapto-4-n-butyl-1,2,4-triazole

3-Mercapto-4-n-butyl-1,2,4-triazole (10 g. or 0.064 mole) was added to a solution of sodium hydroxide (2.6 g. or 0.064 mole) in methanol (200 ml.). The solution was evaporated to dryness under reduced pressure, benzene (100 ml.) was added, and the slurry concentrated to dryness to yield the sodium salt of the triazole. The salt was slurried in benzene (200 ml.) and furoyl chloride (8.5 g. or 0.065 mole) was added and the slurry was heated to reflux for 2 hours. After cooling to room temperature the benzene was washed with water, 5% sodium hydroxide solution, water, dried over sodium sulfate and evaporated to dryness. The solid was recrystallized from benzene to give 3-furoylmercapto-4-n-butyl-1,2,4-triazole melting at 102°–105° C. The structure was confirmed by its infrared spectrum and nuclear magnetic resonance spectrum.

EXAMPLE 125

Preparation of 3-(p-methoxyphenacylmercapto)-4-n-butyl-1,2,4-triazole

To a solution of 3-mercapto-4-n-butyl-1,2,4-triazole (10 g. or 0.063 mole) and sodium hydroxide (2.55 g. or 0.0637 mole) in 200 ml. of methanol was added α-bromo-n-methoxyacetophenone (15.3 g. or 0.067 mole). The reaction mixture was heated at reflux for 16 hours and the solvent removed in vacuum to leave a solid residue. The solid was washed with water and recrystallized from benzene-hexane to give 3-(n-methoxyphenacylmercapto)-4-n-butyl-1,2,4-triazole melting at 79°–82° C. The structure was confirmed by its infrared and nuclear magnetic spectra.

TABLE I 1,2,4-Triazole Examples

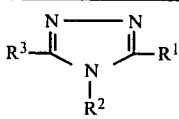

| Ex. No. | $R^1$ | $R^2$ | $R^3$ | Name |
|---|---|---|---|---|
| 1 | H | n-$C_3H_7$ | H | 4-n-propyl-1,2,4-triazole |
| 2 | H | cyclopropyl | H | 4-cyclopropyl-1,2,4-triazole |
| 3 | H | n-$C_4H_9$ | H | 4-n-butyl-1,2,4-triazole |
| 4 | H | i-$C_4H_9$ | H | 4-isobutyl-1,2,4-triazole |
| 5 | H | sec-$C_4H_9$ | H | 4-sec-butyl-1,2,4-triazole |
| 6 | H | t-$C_4H_9$ | H | 4-t-butyl-1,2,4-triazole |
| 7 | H | n-$C_5H_{11}$ | H | 4-n-pentyl-1,2,4-triazole |
| 8 | H | i-$C_5H_{11}$ | H | 4-isopentyl-1,2,4-triazole |
| 9 | H | n-$C_6H_{13}$ | H | 4-n-hexyl-1,2,4-triazole |
| 10 | H | n-$C_8H_{17}$ | H | 4-n-octyl-1,2,4-triazole |
| 11 | H | 2-ethylhexyl | H | 4-(2-ethylhexyl)-1,2,4-triazole |
| 12 | H | n-$C_{10}H_{21}$ | H | 4-n-decyl-1,2,4-triazole |
| 13 | H | n-$C_{12}H_{25}$ | H | 4-n-dodecyl-1,2,4-triazole |
| 14 | H | $CH_3CH=CHCH_2$ | H | 4-(2-butenyl)-1,2,4-triazole |
| 15 | H | propargyl | H | 4-propargyl-1,2,4-triazole |
| 16 | H | 1,1-dimethylpropargyl | H | 4-(1,1-dimethylpropargyl)-1,2,4-triazole |
| 17 | H | $HOCH_2CH_2$ | H | 4-(2-hydroxyethyl)-1,2,4-triazole |
| 18 | H | $HOCH_2CH_2CH_2$ | H | 4-(3-hydroxypropyl)-1,2,4-triazole |
| 19 | H | $C_2H_5CH(OH)CH_2$ | H | 4-(2-hydroxybutyl)-1,2,4-triazole |
| 20 | H | $CH_3CH(OH)CH_2CH_2$ | H | 4-(3-hydroxybutyl)-1,2,4-triazole |
| 21 | H | $HOCH_2CH_2CH_2CH_2$ | H | 4-(4-hydroxybutyl)-1,2,4-triazole |
| 22 | H | $HOCH_2CH(OH)CH_2$ | H | 4-(1,3-dihydroxypropyl)-1,2,4-triazole |
| 23 | H | $CH_3CH(OH)CH(OH)CH_2$ | H | 4-(2,3-dihydroxybutyl)-1,2,4-triazole |
| 24 | H | $C_2H_5OCH_2CH_2$ | H | 4-(2-ethoxyethyl)-1,2,4-triazole |
| 25 | H | $C_6H_5OCH_2CH_2$ | H | 4-(2-phenoxyethyl)-1,2,4-triazole |
| 26 | H | 4-$ClC_6H_4OCH_2CH_2$ | H | 4-(2,4-chlorophenoxy)ethyl)-1,2,4-triazole |
| 27 | H | $CH_3CH_2CH(OCOCH_3)CH_2$ | H | 4-(2-acetoxybutyl)-1,2,4-triazole |
| 28 | H | $CH_3CH(OCOCH_3)CH_2CH_2$ | H | 4-(3-acetoxybutyl)-1,2,4-triazole |
| 29 | H | 2,4-$Cl_2C_6H_3OCH_2CH_2$ | H | 4-(2-(2,4-dichlorophenoxy)ethyl)-1,2,4-triazole |
| 30 | H | 4-$ClC_6H_4SCH_2CH_2$ | H | 4-(2-(4-chlorothiophenoxy)ethyl)-1,2,4-triazole |
| 31 | H | 3,4-$Cl_2C_6H_3SCH_2CH_2$ | H | 4-(2-(3,4-dichlorothiophenoxyethyl)-1,2,4-triazole |
| 32 | H | 4-$CH_3OC_6H_4SCH_2CH_2$ | H | 4-(2-(4-methoxythiophenoxy)ethyl)-1,2,4-triazole |

TABLE I-continued 1,2,4-Triazole Examples

| Ex. No. | R¹ | R² | R³ | Name |
|---|---|---|---|---|
| 33 | H | $C_6H_5CH_2CH_2$ | H | 4-phenethyl-1,2,4-triazole |
| 34 | H | $4\text{-}CH_3OC_6H_4CH_2CH_2$ | H | 4-(4-methoxyphenethyl)-1,2,4-triazole |
| 35 | H | $(C_2H_5)_2NCH_2CH_2$ | H | 4-(2-(diethylamino)ethyl)-1,2,4-triazole |
| 36 | H | 4-imidazolyl-CH₂CH₂ | H | 4-[2-(4-imidazolyl)]-1,2,4-triazole |
| 37 | H | bis(triazinyl)butyl group | H | 4-[4-(1,2,4-triazyl)butyl]-1,2,4-triazole |
| 38 | H | $HOOCCH_2$(HCl Salt) | H | 4-(carboxymethyl)-1,2,4-triazole hydrochloride |
| 39 | H | $CH_3OOCCH_2$ | H | 4-(methoxycarbonylmethyl)-1,2,4-triazole |
| 40 | H | $C_2H_5OOCCH_2(CH_3)CH$ | H | 4-(1-methyl-2-ethoxycarbonylethyl)-1,2,4-triazole |
| 41 | H | $HOOCCH_2CH_2$ | H | 4-(2-carboxyethyl)-1,2,4-triazole |
| 42 | H | $HOOCCH_2CH_2$(HCl Salt) | H | 4-(2-carboxyethyl)-1,2,4-triazole hydrochloride |
| 43 | H | $CH_3OOCH_2CH_2$ | H | 4-(2-methoxycarbonylethyl)-1,2,4-triazole |
| 44 | H | $HOOCCH_2CH_2CH_2$ | H | 4-(3-carboxypropyl)-1,2,4-triazole |
| 45 | H | $CH_3OOCCH_2CH_2CH_2$ | H | 4-(3-methoxycarbonylpropyl)-1,2,4-triazole |
| 46 | H | $CH_3OCH_2CH_2CH_2$ | H | 4-(3-methoxypropyl)-1,2,4-triazole |
| 47 | H | $C_2H_5OCH_2CH_2CH_2$ | H | 4-(3-ethoxypropyl)-1,2,4-triazole |
| 48 | H | $(CH_3)_2CHOCH_2CH_2CH_2$ | H | 4-(3-isopropoxypropyl)-1,2,4-triazole |
| 49 | H | $C_6H_5CH_2$ | H | 4-benzyl-1,2,4-triazole |
| 50 | H | $4\text{-}CH_3OC_6H_4CH_2$ | H | 4-(4-methoxybenzyl)-1,2,4-triazole |
| 51 | H | $4\text{-}ClC_6H_4CH_2$ | H | 4-(4-chlorobenzyl)-1,2,4-triazole |
| 52 | H | $2,4\text{-}Cl_2C_6H_3CH_2$ | H | 4-(2,4-dichlorobenzyl)-1,2,4-triazole |
| 53 | H | $3,4\text{-}Cl_2C_6H_3CH_2$ | H | 4-(3,4-dichlorobenzyl)-1,2,4-triazole |
| 54 | H | $C_6H_5$ | H | 4-phenyl-1,2,4-triazole |
| 55 | H | $3\text{-}ClC_6H_4$(HCl salt) | H | 4-(3-chlorophenyl-)1,2,4-triazole hydrochloride |
| 56 | H | $2,4\text{-}Cl_2C_6H_3$ | H | 4-(2,4-dichlorophenyl)-1,2,4-triazole |
| 57 | H | $3,4\text{-}Cl_2C_6H_3$ | H | 4-(3,4-dichlorophenyl)-1,2,4-triazole |
| 58 | H | $3\text{-}NO_2C_6H_4$ | H | 4-(3-nitrophenyl)-1,2,4-triazole |
| 59 | H | $4\text{-}NO_2C_6H_4$ | H | 4-(4-nitrophenyl)-1,2,4-triazole |
| 60 | H | $4\text{-}CH_3OC_6H_4$ | H | 4-(4-methoxyphenyl)-1,2,4-triazole |
| 61 | H | 4-pyridyl | H | 4-(4-pyridyl)-1,2,4-triazole |
| 62 | H | 2-pyridyl | H | 4-(2-pyridyl)-1,2,4-triazole |
| 63 | H | 5-chloro-2-pyridyl | H | 4-(5-chloro-2-pyridyl)-1,2,4-triazole |
| 64 | H | 4-morpholinyl | H | 4-morpholino-1,2,4-triazole |
| 65 | H | 4-(1,2,4-triazyl) | H | 4-(4-(1,2,4-triazyl)-1,2,4-triazole |
| 66 | H | 3-(1,2,4-triazyl) | H | 4-(3-(1,2,4-triazyl)-1,2,4-triazole |
| 67 | H | 2-pyrimidyl | H | 4-(2-pyrimidyl)-1,2,4-triazole |
| 68 | H | 2-thiazyl | H | 4-(2-thiazyl)-1,2,4-triazole |
| 69 | H | 2-benzothiazyl | H | 4-(2-benzothiazyl)-1,2,4-triazole |
| 70 | H | 2-(4-chlorobenzothiazyl | H | 4-(2-(4-chlorobenzothiazyl)-1,2,4-triazole |
| 71 | H | 2-benzimidazolyl | H | 4-(2-benzimidazolyl)-1,2,4-triazole |
| 72 | H | $CH_3$ | $COOCH_3$ | 3-methoxycarbonyl-4-methyl-1,2,4-triazole |
| 73 | SH | $CH_3$ | H | 3-mercapto-4-methyl-1,2,4-triazole |
| 74 | SH | $C_2H_5$ | H | 3-mercapto-4-ethyl-1,2,4-triazole |
| 75 | SH | $n\text{-}C_3H_7$ | H | 3-mercapto-4-n-propyl-1,2,4-triazole |
| 76 | SH | $n\text{-}C_4H_9$ | H | 3-mercapto-4-n-butyl-1,2,4-triazole |
| 77 | SH | $t\text{-}C_4H_9$ | H | 3-mercapto-4-t-butyl-1,2,4-triazole |
| 78 | SH | $n\text{-}C_5H_{11}$ | H | 3-mercapto-4-n-pentyl-1,2,4-triazole |
| 79 | SH | $n\text{-}C_6H_{13}$ | H | 3-mercapto-4-n-hexyl-1,2,4-triazole |
| 80 | SH | $n\text{-}C_8H_{17}$ | H | 3-mercapto-4-n-octyl-1,2,4-triazole |
| 81 | SH | $t\text{-}C_8H_{17}$ | H | 3-mercapto-4-t-octyl-1,2,4-triazole |
| 82 | SH | $n\text{-}C_{10}H_{21}$ | H | 3-mercapto-4-n-decyl-1,2,4-triazole |
| 83 | SH | cyclohexyl | H | 3-mercapto-4-cyclohexyl-1,2,4-triazole |
| 84 | SH | $C_6H_5CH_2$ | H | 3-mercapto-4-benzyl-1,2,4-triazole |
| 85 | SH | phenyl | H | 3-mercapto-4-phenyl-1,2,4-triazole |
| 86 | SH | $CH_3$ | OH | 3-mercapto-4-methyl-5-hydroxy-1,2,4-triazole |
| 87 | SH | $C_4H_9$ | OH | 3-mercapto-4-n-butyl-5-hydroxy-1,2,4-triazole |
| 88 | SH | $C_6H_5$ | OH | 3-mercapto-4-phenyl-5-hydroxy-1,2,4-triazole |

TABLE I-continued 1,2,4-Triazole Examples

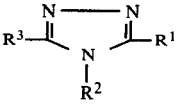

| Ex. No. | $R^1$ | $R^2$ | $R^3$ | Name |
|---|---|---|---|---|
| 89 | SH | $C_4H_9$ | $CH_3$ | 3-mercapto-4-n-butyl-5-methyl-1,2,4-triazole |
| 90 | SH | $CH_3$ | 2-furyl | 3-mercapto-4-methyl-5-(2-furyl)-1,2,4-triazole |
| 91 | SH | $C_4H_9$ | 2-furyl | 3-mercapto-4-n-butyl-5-(2-furyl)-1,2,4-triazole |
| 92 | SH | phenyl | 2-furyl | 3-mercapto-4-phenyl-5-(2-furyl)-1,2,4-triazole |
| 93 | SH | $CH_3$ | COOH | 3-mercapto-4-methyl-5-carboxy-1,2,4-triazole |
| 94 | SH | $C_4H_9$ | COOH | 3-mercapto-4-n-butyl-5-carboxy-1,2,4-triazole |
| 95 | SH | $C_4H_9$ | COOH . $(HOCH_2CH_2)_3N$ | triethanolamine salt of 3-mercapto-4-n-butyl-5-carboxy-1,2,4-triazole |
| 96 | SH | $CH_3$ | $COOCH_3$ | 3-mercapto-4-methyl-5-methoxycarbonyl 1,2,4-triazole |
| 97 | SH | $C_4H_9$ | $COOC_2H_5$ | 3-mercapto-4-n-butyl-5-ethoxycarbonyl 1,2,4-triazole |
| 98 | SNa | $C_4H_9$ | $COOC_2H_5$ | sodium salt of 3-mercapto-4-butyl-5-ethoxycarbonyl-1,2,4-triazole |
| 99 | $-SC(O)NHCH_3$ | $C_4H_9$ | COOH | 3-methylcarbamoylmercapto-4-n-butyl 5-carboxy-1,2,4-triazole |
| 100 | $-SC(O)NHCH_3$ | $C_4H_9$ | COOH . $(HOCH_2CH_2)_3N$ | triethanolamine salt of 3 methylcarbamoylmercapto-4-n-butyl-5-carboxy-1,2,4-triazole |
| 101 | $-SC(S)N(CH_3)_2$ | $C_4H_9$ | COOH | 3-dimethylthiocarbamoylmercapto-4-n-butyl-5-carboxy-1,2,4-triazole |
| 102 | $-SCH_3$ | $C_4H_9$ | H | 3-methylmercapto-4-n-butyl-1,2,4-triazole |
| 103 | $-SC_4H_9-n$ | $C_4H_9$ | H | 3-n-butylmercapto-4-n-butyl-1,2,4-triazole |
| 104 | $-SC_{10}H_{21}-n$ | $C_4H_9$ | H | 3-n-decylmercapto-4-n-butyl-1,2,4-triazole |
| 105 | $-SCH_2CH=CH_2$ | $C_4H_9$ | H | 3-allylmercapto-4-n-butyl-1,2,4-triazole |
| 106 | Product from the cyanoethylation of Example 76 | | | 2-(2-cyanoethyl)-4-n-butyl-1,2,4-triazoline-3-thione |
| 107 | $-SCH_2CH_2OC_2H_5$ | $C_4H_9$ | H | 3-(2-ethoxyethylmercapto-4-n-butyl-1,2,4-triazole |
| 108 | $-SCH_2CH_2OCH_2CH=CH_2$ | $C_4H_9$ | H | 3-(2-allyloxyethylmercapto-4-n-butyl 1,2,4-triazole |
| 109 | $-SCH_2CH_2OC_6H_5$ | $C_4H_9$ | H | 3-(2-phenoxyethylmercapto)-4-n-butyl-1,2,4-triazole |
| 110 | $-SCH(OH)CCl_3$ | $C_4H_9$ | H | 3-(1-hydroxy-2,2,2-trichloro-ethyl-mercapto)-4-n-butyl-1,2,4-triazole |
| 111 | $-SCH_2CONH_2$ | $C_4H_9$ | H | 3-carbamoylmethylmercapto-4-n-butyl-1,2,4-triazole |
| 112 | $-SCH_2C_6H_4OCH_3-4$ | $C_4H_9$ | H | 3-(4-methoxybenzylmercapto)-4-n-butyl-1,2,4-triazole admixed with 4-n-butyl-2-(4-methoxybenzyl)-1,2,4-triazoline-3-thione |
| 114 | $-SCONHCH_3$ | $C_4H_9$ | H | 3-methylcarbamoylmercapto-4-n-butyl-1,2,4-triazole |
| 115 | $-SC(O)CH_3$ | $C_4H_9$ | H | 3-acetylmercapto-4-n-butyl-1,2,4-triazole |
| 116 | $-SC(O)CH_2OCH_3$ | $C_4H_9$ | H | 3-methoxyacetylmercapto-4-n-butyl-1,2,4-triazole |
| 117 | $-SC(O)C_4H_9$ | $C_4H_9$ | H | 3-butyrylmercapto-4-n-butyl-1,2,4-triazole |
| 118 | $-SCOC_6H_4Br-2$ | $C_4H_9$ | H | 3-(2-bromobenzoylmercapto)-4-n-butyl-1,2,4-triazole |
| 119 | $-SCOC_6H_4Br-4$ | $C_4H_9$ | H | 3-(4-bromobenzoylmercapto)-4-n-butyl-1,2,4-triazole |
| 120 | $-SC(O)C_6H_3Cl_23,5$ | $C_4H_9$ | H | 3-(3,5-dichlorobenzoylmercapto-4-n-butyl-1,2,4-triazole |
| 121 | $-SCOC_6H_4OCH_3-4$ | $C_4H_9$ | H | 3-(4-methoxybenzoylmercapto)-4-n-butyl-1,2,4-triazole |
| 122 | $-SCOC_6H_4NO_2-3$ | $C_4H_9$ | H | 3-(3-nitrobenzoylmercapto)-4-n-butyl-1,2,4-triazole |
| 123 | $-SC(O)C_6H_2(OCH_3)_3-3,4,5$ | $C_4H_9$ | H | 3-(3,4,5-trimethoxybenzoylmercapto)-4-n-butyl-1,2,4-triazole |
| 124 | SCOCH=CHCH=CH—O (ring) | $C_4H_9$ | H | 3-furoylmercapto-3-n-butyl-1,2,4-triazole |
| 125 | $-SCH_2COC_6H_4OCH_3-4$ | $C_4H_9$ | H | 3-(p-methoxyphenacylmercapto)-4-n-butyl-1,2,4-triazole |
| 126 | Product from the cyanoethylation of Example 85 | | | 2-(2-cyanoethyl)-4-phenyl-1,2,4-triazoline-3-thione |

TABLE I-continued
1,2,4-Triazole Examples

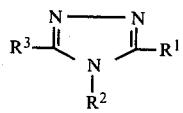

| Ex. No. | R[1] | R[2] | R[3] | Name |
|---|---|---|---|---|
| 127 | —SC$_6$H$_3$(NO$_2$)$_2$-2,4 | C$_4$H$_9$ | H | 3-(2,4-dinitrophenylmercapto)-4-n-butyl-1,2,4-triazole |
| 128 | —SC$_6$H$_3$(NO$_2$)$_2$-2,4 | phenyl | H | 3-(2,4-dinitrophenylmercapto)-4-phenyl-1,2,4-triazole |
| 129 | —SCOC$_6$H$_4$OCH$_3$-4 | phenyl | H | 3-(4-methoxybenzoylmercapto)-4-phenyl-1,2,4-triazole |
| 130 | —SCOC$_6$H$_4$NO$_2$-3 | phenyl | H | 3-(3-nitrobenzoylmercapto)-4-phenyl-1,2,4-triazole |

Example No. 113 is equal to Example No. 127.

TABLE II
Characterization of Examples

| Example No. | Melting Point (°C.) | Empirical Formula | Analysis* or Literature Reference |||| 
|---|---|---|---|---|---|---|
| | | | C | H | N | S |
| 1 | 120–125/.6 mm.$^a$ | C$_5$H$_9$N$_3$ | 52.8 (54.2) | 8.8 (8.1) | 37.2 (37.9) | |
| 2 | 90–93 | C$_5$H$_7$N$_3$ | 54.8 (55.0) | 6.5 (6.4) | 38.4 (38.6) | |
| 3 | 130–142/.2 mm.$^a$ | J. Chem. Soc. (C) 1967, 1665 | | | | |
| 4 | 128–132/.1 mm.$^a$ | C$_6$H$_{11}$N$_3$ | 57.8 (57.6) | 9.2 (8.8) | 33.6 (33.6) | |
| 5 | 130/.1 mm.$^a$ | C$_6$H$_{11}$N$_3$ | 56.5 (57.6) | 9.6 (8.8) | 34.2 (33.6) | |
| 6 | 69–72 | C$_6$H$_{11}$N$_3$ | 51.0 (57.6) | 9.3 (8.8) | 39.5 (33.6) | |
| 7 | 138–148/.1 mm.$^a$ | C$_7$H$_{13}$N$_3$ | 60.3 (60.4) | 8.9 (9.4) | 31.1 (30.2) | |
| 8 | 153–163/.2 mm.$^a$ | C$_7$H$_{13}$N$_3$ | 60.5 (60.4) | 9.7 (9.4) | 30.4 (30.2) | |
| 9 | 145–155/.05 mm.$^a$ | C$_8$H$_{15}$N$_3$ | 62.6 (62.7) | 9.8 (9.8) | 27.2 (27.5) | |
| 10 | 167–174/.01 mm.$^a$ | C$_{10}$H$_{19}$N$_3$ | 65.7 (66.3) | 10.7 (10.6) | 24.4 (23.2) | |
| 11 | 147/.05 mm.$^a$ | C$_{10}$H$_{19}$N$_3$ | 66.0 (66.3) | 10.8 (10.6) | 23.4 (23.2) | |
| 12 | 35–37 | C$_{12}$H$_{23}$N$_3$ | 68.7 (68.9) | 11.1 (11.0) | 20.0 (20.1) | |
| 13 | 51–53 | C$_{14}$H$_{27}$N$_3$ | 70.5 (70.9) | 10.6 (11.5) | 17.5 (17.7) | |
| 14 | 136/.05 mm.$^a$ | C$_6$H$_9$N$_3$ | 57.6 (58.5) | 7.2 (7.3) | 34.5 (34.1) | |
| 15 | 145–153/.05 mm.$^a$ | C$_5$H$_5$N$_3$ | 53.4 (56.1) | 4.7 (4.7) | 39.4 (39.2) | |
| 16 | 108–111 | C$_7$H$_9$N$_3$ | 62.1 (63.1) | 6.8 (6.7) | 31.1 (31.2) | |
| 17 | 79–82 | C$_4$H$_7$N$_3$O | 42.4 (42.5) | 6.0 (6.2) | 37.6 (37.2) | |
| 18 | semisolid | C$_5$H$_9$N$_3$O | 46.8 (47.2) | 7.6 (7.1) | 29.9 (33.0) | |
| 19 | 96–99 | C$_6$H$_{11}$N$_3$O | 51.3 (51.0) | 7.8 (7.8) | 29.9 (29.8) | |
| 20 | 75–76 | C$_6$H$_{11}$N$_3$O | 51.0 (51.0) | 7.8 (7.8) | 29.8 (29.8) | |
| 21 | Conc. | C$_6$H$_{11}$N$_3$O | Structure confirmed by MS & NMR$^b$ | | | |
| 22 | 97–98 | C$_5$H$_9$N$_3$O$_2$ | 41.9 (42.0) | 6.3 (6.2) | 29.4 (29.4) | |
| 23 | 109–110 | C$_6$H$_{11}$N$_3$O$_2$ | 46.0 (45.8) | 7.0 (7.0) | 26.4 (26.8) | |
| 24 | 145–149/.05 mm.$^a$ | C$_6$H$_{11}$N$_3$O | 49.5 (51.0) | 7.3 (7.9) | 29.8 (29.8) | |
| 25 | 75–78 | C$_{10}$H$_{11}$N$_3$O | 62.0 (63.5) | 5.9 (5.9) | 21.5 (22.2) | |
| 26 | 74–75 | C$_{10}$H$_{10}$ClN$_3$O | 50.8 (53.8) | 4.4 (4.5) | 20.9 (18.9) | |
| 27 | oil | C$_8$H$_{13}$N$_3$O$_2$ | 51.4 (52.5) | 7.2 (7.1) | 22.6 (22.9) | |
| 28 | oil | C$_8$H$_{13}$N$_3$O$_2$ | 52.2 (52.5) | 7.2 (7.1) | 22.3 (22.9) | |
| 29 | 115–117 | C$_{10}$H$_9$Cl$_2$N$_3$O | 46.6 (46.5) | 3.7 (3.5) | 16.3 (16.3) | |
| 30 | 73–75 | C$_{10}$H$_{10}$ClN$_3$S | 49.9 (50.3) | 4.2 (4.2) | 14.7 (14.7) | |
| 31 | 127–129 | C$_{10}$H$_9$Cl$_2$N$_3$S | 43.8 (43.7) | 3.5 (3.3) | 15.1 (15.3) | |
| 32 | 74–76 | C$_{11}$H$_{13}$N$_3$OS | 56.2 (56.2) | 5.7 (5.5) | 18.1 (17.9) | |
| 33 | 182–185/.02 mm.$^a$ | C$_{10}$H$_{11}$N$_3$ | 69.0 (69.3) | 6.8 (6.4) | 24.2 (24.3) | |
| 34 | 210–220/.1 mm.$^a$ | C$_{11}$H$_{13}$N$_3$O | 64.5 (65.0) | 6.5 (6.5) | 20.6 (20.7) | |
| 35 | 155–168/.05 mm.$^a$ | C$_8$H$_{16}$N$_4$ | 56.7 (57.1) | 10.6 (9.6) | 34.4 (33.3) | |
| 36 | 147–149 | C$_7$H$_8$N$_5$ | 50.8 (51.5) | 5.7 (5.6) | 42.7 (42.9) | |
| 37 | 131–134 | C$_8$H$_{12}$N$_6$ | 49.7 (50.0) | 6.4 (6.3) | 43.6 (43.7) | |
| 38 | 169–171 | C$_4$H$_5$N$_3$O$_2$ · HCl | 29.4 (29.4) | 3.8 (3.7) | 25.8 (25.7) | |
| 39 | 98–99 | C$_5$H$_7$N$_3$O | 42.5 (42.5) | 5.1 (5.0) | 29.7 (29.8) | |
| 40 | 170–172/.2 mm. | C$_8$H$_{13}$N$_3$O$_2$ | 50.3 (52.4) | 6.5 (7.1) | 25.7 (22.9) | |
| 41 | 174–176 | C$_5$H$_7$N$_3$O$_2$ | 42.4 (42.6) | 5.0 (4.9) | 29.6 (29.8) | |
| 42 | 148–150 | C$_5$H$_7$N$_3$O$_2$ · HCl | 33.0 (33.9) | 4.3 (4.5) | 22.2 (23.7) | |
| 43 | oil | C$_6$H$_9$N$_3$O$_2$ | Structure confirmed by MS & NMR | | | |
| 44 | 137–139 | C$_6$H$_9$N$_3$O$_2$ | 46.3 (46.5) | 5.8 (5.8) | 26.7 (27.1) | |
| 45 | oil | C$_7$H$_{11}$N$_3$O$_2$ | Structure confirmed by MS & NMR | | | |
| 46 | 130–140/.05 mm.$^a$ | C$_6$H$_{11}$N$_3$O | 51.5 (51.0) | 8.3 (7.8) | 30.2 (29.8) | |
| 47 | 125–132/.2 mm.$^a$ | C$_7$H$_{13}$N$_3$O | 53.2 (54.2) | 8.7 (8.4) | 27.6 (27.1) | |
| 48 | 156–164/.2 mm.$^a$ | C$_8$H$_{15}$N$_3$O | 59.6 (56.8) | 8.3 (8.9) | 25.5 (24.8) | |
| 49 | 112–114 | | J. Chem. Soc. (C) 1967, 1666 | | | |
| 50 | 101–103 | C$_{10}$H$_{11}$N$_3$O | 62.9 (63.4) | 5.9 (5.9) | 22.1 (22.2) | |
| 51 | 200–203/.05 mm.$^a$ | C$_9$H$_8$ClN$_3$ | 55.7 (55.8) | 4.6 (4.1) | 21.7 (21.7) | |
| 52 | 169–171 | C$_9$H$_7$Cl$_2$N$_3$ | 47.7 (47.5) | 3.4 (3.1) | 18.4 (18.4) | |
| 53 | 133–135 | C$_9$H$_7$Cl$_2$N$_3$ | 47.6 (47.5) | 3.2 (3.1) | 18.5 (18.4) | |
| 54 | 118–121 | C$_8$H$_7$N$_3$ | J. Chem. Soc. 1967, 1664 | | | |
| 55 | 196–200 | C$_8$H$_6$ClN$_3$ · HCl | J. Med. Pharm. Chem. 5, 383 (1962) | | | |
| 56 | 203–206 | C$_8$H$_5$Cl$_2$N$_3$ | J. Med. Pharm. Chem. 5, 383 (1962) | | | |

TABLE II-continued
Characterization of Examples

| Example No. | Melting Point (°C.) | Empirical Formula | Analysis* or Literature Reference | | | |
|---|---|---|---|---|---|---|
| | | | C | H | N | S |
| 57 | 172–174 | C$_8$H$_5$Cl$_2$N$_3$ | 45.1 (44.9) | 2.3 (2.3) | 19.4 (19.6) | |
| 58 | 242–245 | C$_8$H$_6$N$_4$O$_2$ | 50.4 (50.6) | 3.1 (3.1) | 30.0 (29.5) | |
| 59 | >300 | C$_8$H$_6$N$_4$O$_2$ | J. Med. Pharm. Chem. 5, 383 (1962) | | | |
| 60 | 108–110 | C$_9$H$_9$N$_3$O | J. Med. Pharm. Chem. 5, 383 (1962) | | | |
| 61 | 230–231 | C$_7$H$_6$N$_4$ | 57.8 (57.5) | 4.0 (4.1) | 38.1 (38.4) | |
| 62 | 162–163 | C$_7$H$_6$N$_4$ | J. Org. Chem. 18, 1368 (1953) | | | |
| 63 | 217–218 | C$_7$H$_5$ClN$_4$ | 47.0 (46.5) | 2.8 (2.8) | 30.8 (31.0) | |
| 64 | 148–150 | C$_6$H$_{10}$N$_4$O | 44.8 (46.8) | 6.7 (6.5) | 35.4 (36.3) | |
| 65 | 276–277 | C$_4$H$_4$N$_6$ | J. Chem. Soc. 1967, 1666 | | | |
| 66 | 190–195 | C$_4$H$_4$N$_6$ | J. Org. Chem. 18, 1368 (1953) | | | |
| 67 | 246–249 | C$_6$H$_5$N$_5$ | 49.2 (49.0) | 3.3 (3.4) | 47.6 (47.6) | |
| 68 | 127–129 | C$_5$H$_4$N$_4$S | 39.5 (39.5) | 2.5 (2.7) | 37.2 (36.8) | |
| 69 | 199–201 | C$_9$H$_6$N$_4$S | 54.0 (53.5) | 3.3 (3.0) | 27.6 (27.7) | |
| 70 | 187–189 | C$_9$H$_5$ClN$_4$S | 46.6 (45.7) | 2.7 (2.1) | 24.1 (23.7) | |
| 71 | 303–305 | C$_9$H$_7$N$_5$ | 57.7 (58.4) | 4.2 (3.8) | 35.9 (37.8) | |
| 72 | 85–86 | C$_5$H$_7$N$_3$O$_2$ | 42.8 (42.6) | 5.2 (4.9) | 30.1 (29.8) | |
| 73 | 163–165 | | Berichte 29, 2489 (1896) | | | |
| 74 | 98–100 | | Berichte 29, 2487 (1896) | | | |
| 75 | 74–75 | C$_5$H$_9$N$_3$S | 42.2 (41.9) | 6.3 (6.3) | 29.0 (29.4) | 22.2 (22.3) |
| 76 | 67–69 | C$_6$H$_{11}$N$_3$S | 46.0 (45.8) | 7.1 (7.0) | 26.9 (26.8) | 20.25 (20.4) |
| 77 | 199–201 | C$_6$H$_{11}$N$_3$S | 45.8 (45.8) | 7.1 (7.0) | 26.9 (26.8) | 20.2 (20.4) |
| 78 | 38–40 | C$_7$H$_{13}$N$_3$S | 49.0 (49.1) | 7.4 (7.6) | 24.3 (24.6) | 18.9 (18.7) |
| 79 | 56–57 | C$_8$H$_{15}$N$_3$S | 5.18 (51.9) | 7.7 (8.1) | 22.8 (22.7) | 17.4 (17.3) |
| 80 | 61–62 | C$_{10}$H$_{19}$N$_3$S | 56.6 (56.4) | 8.9 (8.9) | 19.6 (19.7) | 15.2 (15.0) |
| 81 | 182–184 | C$_{10}$H$_{19}$N$_3$S | 56.6 (56.4) | 9.0 (8.9) | 20.0 (19.7) | 15.1 (15.0) |
| 82 | 67–68 | C$_{12}$H$_{23}$N$_3$S | 60.0 (59.7) | 9.7 (9.6) | 17.6 (17.4) | 13.3 (13.3) |
| 83 | 164–166 | C$_8$H$_{13}$N$_3$S | 52.7 (52.5) | 7.2 (7.1) | 22.8 (23.0) | 17.8 (17.5) |
| 84 | 118–120 | | Saikochi and Kanaoko Chem. Abstracts 56, 7305 | | | |
| 85 | 171–173 | | Compt. rend. 248, 1677 (1959) | | | |
| 86 | 215–217 (dec.) | C$_3$H$_5$N$_3$OS | J. Org. Chem. 23, 619 (1958) | | | |
| 87 | 152–154 | C$_6$H$_{11}$N$_3$OS | J. Org. Chem. 23, 619 (1958) | | | |
| 88 | 135–136 | | Compt. rend. 248, 1677 (1959) | | | |
| 89 | 101–102 | C$_7$H$_{13}$N$_3$S | 48.9 (49.1) | 7.8 (7.6) | 24.2 (24.6) | 19.1 (18.7) |
| 90 | 192–194 | C$_7$H$_7$N$_3$OS | 46.7 (46.4) | 3.9 (3.9) | 23.5 (23.2) | 17.5 (17.7) |
| 91 | 103–105 | C$_{10}$H$_{13}$N$_3$OS | 53.7 (53.8) | 5.8 (5.8) | 18.9 (18.8) | 14.8 (14.4) |
| 92 | 215 | C$_{12}$H$_9$N$_3$OS | 59.2 (59.3) | 3.95 (3.7) | 17.2 (17.3) | 13.2 (13.1) |
| 93 | 158–160 | C$_4$H$_5$N$_3$O$_2$S | 30.4 (30.2) | 3.4 (3.1) | 26.7 (26.4) | 19.9 (20.1) |
| 94 | 108–110 | C$_7$H$_{11}$N$_3$O$_2$S . H$_2$O | 38.1 (38.4) | 5.9 (5.9) | 19.1 (19.2) | 14.7 (14.6) |
| 95 | 132–134 | C$_{13}$H$_{26}$N$_4$O$_2$S | 51.8 (51.7) | 8.8 (8.7) | 18.8 (18.5) | 10.9 (10.6) |
| 96 | 129–131 | C$_5$H$_7$N$_3$O$_2$S | 33.6 (34.7) | 3.9 (4.1) | 24.9 (24.2) | 19.0 (18.5) |
| 97 | soft solid | C$_9$H$_{15}$N$_3$O$_2$S | 46.7 (47.1) | 6.7 (6.6) | 18.6 (18.3) | 14.4 (14.0) |
| 98 | hygroscopic solid | | | | | |
| 99 | 106–107 | C$_9$H$_{14}$N$_4$O$_3$S | 41.8 (40.9) | 6.3 (6.2) | 19.9 (19.2) | 11.4 (10.9) |
| 100 | concentrate | C$_{15}$H$_{29}$N$_5$O$_3$S | 50.0 (50.6) | 9.5 (8.1) | 20.9 (19.5) | 7.8 (8.9) |
| 101 | brown oil | | | | | |
| 102 | 128–131/2 mm.$^a$ | C$_7$H$_{13}$N$_3$S | 49.1 (49.1) | 7.6 (7.6) | 24.6 (24.6) | 19.0 (18.7) |
| 103 | 140–155/.5 mm.$^a$ | C$_{10}$H$_{19}$N$_3$S | 56.1 (56.2) | 8.9 (9.0) | 20.2 (19.7) | 15.1 (15.2) |
| 104 | 195–205/.1 mm.$^a$ | C$_{16}$H$_{31}$N$_3$S | 64.7 (64.7) | 10.7 (10.5) | 14.5 (14.1) | 10.6 (10.8) |
| 105 | 136–152/.06 mm.$^a$ | C$_9$H$_{15}$N$_3$S | 54.3 (54.8) | 8.0 (7.7) | 21.3 (21.3) | 16.4 (16.2) |
| 106 | 168–175/2 mm.$^a$ | C$_9$H$_{14}$N$_4$S | 51.2 (51.4) | 6.8 (6.7) | 26.65 (26.7) | 15.1 (15.2) |
| 107 | 147–155/1 mm.$^a$ | C$_{10}$H$_{19}$N$_3$OS | 52.7 (52.3) | 8.2 (8.3) | 18.8 (18.4) | 14.45 (14.0) |
| 108 | 160–170/.05 mm.$^a$ | C$_{10}$H$_{17}$N$_3$OS | 52.8 (52.9) | 7.7 (7.5) | 18.5 (18.5) | 14.1 (14.1) |
| 109 | 220–230/.25 mm.$^a$ | C$_{14}$H$_{19}$N$_3$OS | 60.9 (60.6) | 7.3 (6.9) | 15.05 (15.2) | 10.9 (11.5) |
| 110 | 95–97 | C$_8$H$_{12}$Cl$_3$N$_3$OS | 31.8 (31.6) | 4.2 (3.95) | 13.95 (13.8) | 10.8 (10.5) |
| 111 | 74–76 | C$_8$H$_{14}$N$_4$OS | 45.6 (44.8) | 6.3 (6.5) | 26.7 (26.2) | 14.3 (15.0) |
| 112 | 190–205/.03 mm.$^a$ | C$_{14}$H$_{19}$N$_3$OS | 60.6 (60.6) | 7.1 (6.9) | 16.0 (15.2) | 10.95 (11.5) |
| 113 | 105–107 | C$_{12}$H$_{13}$N$_5$O$_4$S | 44.8 (44.6) | 4.3 (4.0) | 21.5 (21.7) | 20.1 (19.8) |
| 114 | 112–114 | C$_8$H$_{14}$N$_4$OS | 45.1 (44.9) | 6.7 (6.6) | 26.2 (26.2) | 14.3 (14.9) |
| 115 | 123–126 | C$_8$H$_{13}$N$_3$OS | 48.1 (48.3) | 6.4 (6.6) | 21.0 (21.0) | 16.1 (16.1) |
| 116 | 118–120 | C$_9$H$_{15}$N$_3$O$_2$S | 47.2 (47.2) | 6.3 (6.6) | 18.3 (18.3) | 12.6 (14.1) |
| 117 | 109–112 | C$_{10}$H$_{17}$N$_3$OS | 53.5 (52.9) | 7.4 (7.5) | 18.8 (18.7) | 12.6 (14.1) |

*The number in parenthesis represents the theoretical value as calculated from the empirical formula
$^a$ = Boiling point in °C.
$^b$MS = mass spectra and NMR = Nuclear Magnetic Resonance.

Characterization of Examples

| Example No. | Melting Point (°C.) | Empirical Formula | Analysis* or Literature Reference | | | |
|---|---|---|---|---|---|---|
| | | | C | H | N | S |
| 118 | 143–144 | C$_{13}$H$_{14}$BrN$_3$OS | 46.2 (45.9) | 4.05 (14.1) | 12.4 (12.3) | 9.5 (9.4) |
| 119 | 160–162 | C$_{13}$H$_{14}$BrN$_3$OS | 45.8 (45.9) | 4.0 (4.1) | 12.2 (12.3) | 9.5 (9.4) |
| 120 | 154–156 | C$_{13}$H$_{13}$Cl$_2$N$_3$OS | 48.2 (47.4) | 4.0 (3.9) | 12.7 (12.7) | 9.7 (9.7) |
| 121 | 94–96 | C$_{14}$H$_{17}$N$_3$O$_2$S | 57.7 (57.7) | 5.8 (5.9) | 14.4 (14.4) | 11.0 (11.0) |
| 122 | 114–116 | C$_{13}$H$_{14}$N$_4$O$_3$S | 51.0 (51.0) | 5.2 (4.6) | 18.3 (18.3) | 10.5 (10.4) |
| 123 | 162–165 | C$_{16}$H$_{21}$N$_3$O$_4$S | 54.3 (54.7) | 5.9 (6.0) | 11.7 (11.9) | 9.1 (9.1) |
| 124 | 102–5 | C$_{11}$H$_{13}$N$_3$O$_2$S | 52.7 (52.6) | 5.5 (5.2) | 16.6 (16.7) | 12.7 (12.8) |

-continued

| | | Characterization of Examples | | | | |
|---|---|---|---|---|---|---|
| Example No. | Melting Point (°C.) | Empirical Formula | Analysis* or Literature Reference | | | |
| | | | C | H | N | S |
| 125 | 79–82 | $C_5H_{19}N_3O_2S$ | 58.1 (59.1) | 6.4 (6.3) | 13.6 (13.8) | 10.4 (10.5) |
| 126 | 100–102 | Chemical Abstracts 63, 13242 (1965) | | | | |
| 127 | 105–107 | $C_{12}H_{13}N_5O_4S$ | 44.8 (44.6) | 4.3 (4.0) | 21.5 (21.7) | 10.0 (9.9) |
| 128 | 248–250 | $C_{14}H_9N_5O_4S$ | 49.0 (49.0) | 2.8 (2.6) | 20.3 (20.4) | 9.4 (9.3) |
| 129 | 174–176 | $C_{16}H_{13}N_3O_2S$ | 61.9 (61.8) | 4.25 (4.2) | 13.5 (13.5) | 10.5 (10.3) |
| 130 | 143–146 | $C_{15}H_{10}N_4O_3S$ | 55.35 (55.2) | 3.25 (3.1) | 17.2 (17.2) | 9.9 (9.8) |

*The nubmer in parenthesis represents the theoretical value as calculated from the empirical formula
$^a$= Boiling point in °C.
$^b$MS = mass spectra and NMR = Nuclear Magnetic Resonance.

Among the structures of this invention which are fungicidal the preferred compounds are those which are novel. Novel structures within this invention may be represented by the structure

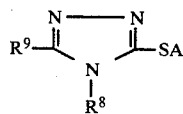
(XII)

wherein A is
(a) hydrogen,
(b) alkyl groups of 1 to 12 carbon atoms optionally substituted by (1) halogen, preferably chlorine, (2) lower alkoxy, (3) cyano, (4) carbamyl, (5) alkenyloxy of 3 to 6 carbon atoms, (6) phenoxy, (7) phenyl, (8) lower alkoxy, lower alkyl, halo preferably chloro or nitro substituted phenyl, (9) benzoyl and (10) halo preferably chloro, lower alkoxy, lower alkyl or nitro substituted benzoyl,
(c) alkenyl of 3 to 6 carbon atoms,
(d) the group $-C(X)R^4$ wherein X is O or S and $R^4$ is selected from the group consisting of lower alkyl, methoxy substituted lower alkyl, phenyl, lower alkyl substituted phenyl, lower alkoxy substituted phenyl, halo and nitro substituted phenyl, furoyl, and the $-NR^5R^6$ wherein $R^5$ and $R^6$ may be hydrogen or lower alkyl groups,
(e) the group $-CH(OH)R^7$ wherein $R^7$ is hydrogen, lower alkyl or lower halo-substituted alkyl,
(f) the group

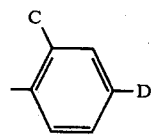

wherein C and D are hydrogen and a meta-directing group such as cyano, nitro, sulfonic acid and sulfonic acid derivatives with the proviso that only one of C and D may be hydrogen,
(g) salt-forming metals such as the alkali and alkaline earth metals, cadmium, copper, iron, manganese, nickel and zinc;
When A is hydrogen $R^8$ is alkyl of 3–18 carbon atoms which may be substituted with one or more halo preferably chloro, lower alkoxy, hydroxy or nitro groups; and cycloalkyl of 3–8 carbon atoms which may be substituted with one or more halo preferably chloro, hydroxy or nitro groups;
When A is methyl $R^8$ is alkyl of 3–18 carbon atoms which may be substituted with one or more halo preferably chloro, lower alkoxy, hydroxy or nitro groups; benzyl and benzyl in which the phenyl group is substituted with lower alkyl, halo preferably chloro and nitro groups;
When A is carbamoylmethyl, benzyl, nitrobenzyl or sodium $R^8$ is alkyl of 1–18 carbon atoms which may be substituted with one or more halo preferably chloro, lower alkoxy, hydroxy or nitro groups; benzyl and benzyl in which the phenyl group is substituted with lower alkyl, halo preferably chloro and nitro groups;
When A is all other values $R^8$ is alkyl of 1–18 carbon atoms which may be substituted with one or more halo preferably chloro, lower alkoxy, hydroxy or nitro groups; cycloalkyl of 3–8 carbon atoms which may be substituted with one or more halo preferably chloro, hydroxy or nitro groups; benzyl, benzyl substituted in the phenyl group with lower alkyl, halo preferably chloro, and nitro groups; phenyl and lower alkyl, halo preferably chloro, and nitro substituted phenyl; and
$R^9$ is hydrogen, lower alkyl, furyl and the group $-COOB$ wherein B is hydrogen, lower alkyl, ammonium, ammonium monosubstituted with lower alkyl or lower hydroxyalkyl, ammonium disubstituted with lower alkyl or lower hydroxyalkyl, ammonium trisubstituted with lower alkyl or lower hydroxyalkyl, quaternary ammonium and salt-forming metals; and acid salts of the compounds of Formula XII which are basic.

Other novel structures within the scope of this invention and which are preferred fungicides may be depicted by the formula

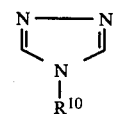
(XIII)

wherein $R^{10}$ is
(a) alkyl, straight or branched, of 3 to 18 carbon atoms, exclusive of n-butyl, which may be substituted with hydroxy, lower alkoxy, lower alkylamino, di(lower alkyl) amino phenyl, methoxy-substituted phenyl, an imidazoyl group, a 1,2,4-triazyl group or a COY group wherein Y is hydroxy or lower alkoxy,
(b) alkenyl of 3 to 6 carbon atoms,
(c) alkynyl of 3 to 6 carbon atoms,
(d) cycloalkyl of 3 to 8 carbon atoms, and
(e) a heterocyclic group selected from the group consisting of 2-thiazyl, 2-pyrimidyl, morpholino, 2-benzothiazyl, and their chlorinated derivatives and chlorinated 2-pyridyl.

Other novel structures within the scope of this invention may be depicted by the formula

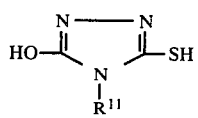

wherein $R^{11}$ is alkyl of greater than 7 carbon atoms which may be substituted with one or more halo preferably chloro, lower alkoxy, hydroxy or nitro groups.

Typical compounds within the scope of Formulas XII, XIII and XIV include the following:
4-isopropyl-1,2,4-triazole
4-sec-butyl-1,2,4-triazole
4-n-pentyl-1,2,4-triazole
4-dodecyl-1,2,4-triazole
4-octadecyl-1,2,4-triazole
3-mercapto-4-isobutyl-1,2,4-triazole
3-mercapto-4-isopentyl-1,2,4-triazole
3-mercapto-4-undecyl-1,2,4-triazole
3-mercapto-4-(4-chlorobutyl)-1,2,4-triazole
3-mercapto-4-(4-methoxypropyl)-1,2,4-triazole
3-mercapto-4-(2-hydroxybutyl)-1,2,4-triazole
3-mercapto-4-(4-nitrobutyl)-1,2,4-triazole
3-mercapto-4-cyclopropyl-1,2,4-triazole
3-methylmercapto-4-(3-chloropropyl)-1,2,4-triazole
3-ethylmercapto-4-butyl-1,2,4-triazole
3-butylmercapto-4-(2-chloropropyl)-1,2,4-triazole
3-chloromethylmercapto-4-butyl-1,2,4-triazole
3-(2-hydroxyethylmercapto)-4-butyl-1,2,4-triazole
3-(2-cyanoethylmercapto)-4-butyl-1,2,4-triazole
3-(2-nitroethylmercapto)-4-butyl-1,2,4-triazole
3-[2-(4-chlorophenoxy)ethylmercapto]-4-butyl-1,2,4-triazole
3-[2-(2-methylphenoxy)ethylmercapto]-4-butyl-1,2,4-triazole
3-[2-(3-nitrophenoxy)ethylmercapto]-4-butyl-1,2,4-triazole
3-benzylmercapto-4-butyl-1,2,4-triazole
3-(4-chlorobenzylmercapto)-4-butyl-1,2,4-triazole
3-(dodecylbenzylmercapto)-4-butyl-1,2,4-triazole
3-phenacylmercapto-4-butyl-1,2,4-triazole
3-(3,5-dichlorophenacylmercapto)-4-butyl-1,2,4-triazole
3-benzoylmercapto-4-chloropropyl-1,2,4-triazole
3-(3-nitrobenzoylmercapto)-4-benzyl-1,2,4-triazole
3-carbamoylmercapto-4-benzyl-1,2,4-triazole
3-methylcarbamoylmercapto-4-(4-chlorobenzyl)-1,2,4-triazole
3-dimethylcarbamoylmercapto-4-(2-chloroethyl)-1,2,4-triazole
3-carbamoylmethylmercapto-4-(3-chloropropyl)-1,2,4-triazole
3-carbamoylmethylmercapto-4-(2-methoxybenzyl)-1,2,4-triazole
3-carbamoylmethylmercapto-4-(4-nitrobenzyl)-1,2,4-triazole
3-methylcarbamoylmethylmercapto-4-butyl-1,2,4-triazole
3-hydroxyethylmercapto-4-(2-chlorobutyl)-1,2,4-triazole
3-chloromethylmercapto-4-butyl-1,2,4-triazole
3-(1-hydroxy-2,4-dichloroethylmercapto)-4-(2-chloropropyl)-1,2,4-triazole
3-(2-nitrophenylmercapto)-4-(3-bromopropyl)-1,2,4-triazole
3-(2-cyanophenylmercapto)-4-butyl-1,2,4-triazole
3-(4-sulfonamidophenylmercapto)-4-benzyl-1,2,4-triazole
3-(4-nitrophenylmercapto)-4-(4-chlorobenzyl)-1,2,4-triazole
3-furoylmercapto-4-(3-chloropropyl)-1,2,4-triazole
3-furoylmercapto-4-(2-chlorobenzyl)-1,2,4-triazole
3-mercapto-4-(2-chloroethyl)-5-methyl-1,2,4-triazole
3-mercapto-4-(2-chlorobenzyl)-5-furyl-1,2,4-triazole
3-mercapto-4-(4-chlorobutyl)-5-butyl-1,2,4-triazole
3-mercapto-4-(2-bromopropyl)-5-(2-hydroxyethyl)-1,2,4-triazole
3-mercapto-4-benzyl-5-(2-nitroethyl)-1,2,4-triazole
3-mercapto-4-cyclopentyl-5-hydroxymethyl-1,2,4-triazole
3-methylmercapto-4-butyl-5-methyl-1,2,4-triazole
3-ethylmercapto-4-(3-chloropropyl)-5-chloromethyl-1,2,4-triazole
3-(2-chloroethylmercapto)-4-(2-chloroethyl)-5-carboxy-1,2,4-triazole
3-carbamoylmercapto-4-(3-methoxypropyl)-5-carboxy-1,2,4-triazole
3-(3-methoxypropylmercapto)-4-(4-chlorobenzyl)-5carboxy-1,2,4-triazole
3-(4-nitrophenylmercapto)-4-(3-bromopropyl)-5-carboxy-1,2,4-triazole
3-(4-methylbenzoylmercapto)-4-octyl-5-hydroxy-1,2,4-triazole
3-mercapto-4-(2-hydroxyethyl)-5-hydroxy-1,2,4-triazole
3-mercapto-4-(2-chlorobutyl)-5-hydroxy-1,2,4-triazole The 1,2,4-triazoles of this invention and salts thereof possess biocidal properties and in this respect are particularly useful as agricultural fungicides. As such, they may be applied to various loci such as the seed, the soil or the foliage. For such purposes the 1,2,4-triazoles may be used in the technical or pure form as prepared, as solutions or as formulations. The compounds are usually taken up in a carrier or are formulated so as to render them suitable for subsequent dissemination as pesticides. For example, the 1,2,4-triazoles may be formulated as wettable powders, emulsifiable concentrates, dusts, granular formulations, aerosols, flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art may be found in the John W. McCutcheon, Inc. publication "Detergents and Emulsifiers 1967 Annual". Of course the surfactant should be selected relative to the specific triazole. In some instances the cationic 1,2,4-triazole salts may be incompatible with anionic surfactants and the anionic 1,2,4-triazole salts may be incompatible with cationic surfactants.

In case the 1,2,4-triazole compound is water-soluble, it may be dissolved directly in water to provide an aqueous solution for application. Similarly, the compounds of this invention may be dissolved in a water-miscible liquid, such as methanol, ethanol, isopropanol, acetone, dimethylformamide or dimethyl sulfoxide or mixtures of these with water and such solutions extended with water. The concentration of the solution may vary from 2% to 98% with a preferred range being 25% to 75%.

For the preparation of emulsifiable concentrates, the compound may be dissolved in organic solvents, such as xylene, pine oil, orthodichlorobenzene, methyl oleate, or a mixture of solvents, together with an emulsifying agent which permits dispersion of the pesticide in water. The concentration of the active ingredient in emulsion concentrates is usually 10% to 25% and in flowable emulsion concentrates, this may be as high as 75%.

Wettable powders suitable for spraying, may be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%.

Dusts are prepared by mixing the 1,2,4-triazoles with finely divided inert solids which may be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The 1,2,4-triazoles can be applied as fungicidal sprays by methods commonly employed, such as conventional high-gallonage hydraulic sprays, low gallonage sprays, airblast spray, aerial sprays and dusts. The dilution and rate of application will depend upon the type of equipment employed, the method of application and disease to be controlled, but the amount is usually 0.1 lb. to 25 lbs. per acre of the active ingredient.

As a seed treatment, the amount of toxicant coated on the seed is usually at a dosage rate of about 0.1 to 20 ounces per hundred pounds of seed. As a soil fungicide the chemical may be incorporated in the soil or applied to the surface usually at a rate of 0.1 to 25 lbs. per acre. As a foliar fungicide the toxicant is usually applied to growing plants at a rate of 0.25 to 10 pounds per acre.

The substituted 1,2,4-triazoles of this invention are also of interest when mixed with fertilizer and fertilizing materials. Such mixtures with fertilizers may be made in a variety of ways. For example, liquid formulations may be sprayed onto particles of mixed fertilizer or of fertilizer ingredients such as ammonium sulfate, ammonium nitrate, ammonium phosphate, potassium chloride or sulfate, calcium phosphate or urea, singly or in admixture. Also, the toxicants and the solid fertilizing materials may be admixed in mixing or blending equipment. Similarly, a solution of toxicants in a volatile solvent may be applied to particles of fertilizer or fertilizer ingredients. A particularly useful form in which the toxicants are incorporated with fertilizers is in granular formulations. This type of solid composition serves a dual purpose in providing fertilizing material for the rapid growth of desired plants and at the same time helps control fungal diseases in one operation without the necessity of separate applications.

The compounds of this invention were evaluated as foliar fungicides for the control of wheat leaf rust, *Puccinia recondita*. In this test aqueous sprays were applied to about one week old wheat seedlings and the plants were allowed to dry. They were then inoculated with standard spore suspension of the wheat leaf rust organism containing approximately 25,000 spores per ml. The plants were then held under standard conditions for the disease to develop. After about 7-9 days, lesions were counted and compared to those on untreated plants. The percent disease control was calculated. In a related test in order to dtermine the persistency of the sprays, the treated plants were rained upon for varying times in a standard rain machine in which six minutes of rain was equal to about one inch of rain. Table III gives the results. Dashes indicate no data.

TABLE III

Wheat Leaf Rust Control by Foliar Application

| Example No. | % Control (without rain) 1 lb. | % Control (without rain) 0.25 lb. | % Control (with 1" of rain) 1 lb. | % Control (with 1" of rain) 0.25 lb. |
|---|---|---|---|---|
| 1 | 100 | 100 | 100 | 87 |
| 2 | 90 | 90 | 0 | 40 |
| 3 | 100 | 100 | 100 | 100 |
| 4 | 95 | 95 | 60 | 30 |
| 5 | 99 | 97 | 69 | 78 |
| 6 | 100 | 100 | 95 | 95 |
| 7 | 100 | 100 | 100 | 100 |
| 8 | 99 | 98 | 100 | 98 |
| 9 | 100 | 100 | 100 | 100 |
| 12 | 100 | 57 | 78 | 48 |
| 13 | 60 | 20 | 30 | 0 |
| 14 | 100 | 100 | 100 | 99 |
| 15 | 100 | 100 | 100 | 99 |
| 16 | 0 | 0 | 0 | 0 |
| 17 | 5 | 60 | 0 | 0 |
| 18 | 0 | 0 | 0 | 0 |
| 19 | 65 | 65 | 0 | 0 |
| 20 | 0 | 0 | 0 | 0 |
| 21 | 10 | 10 | 0 | 0 |
| 22 | 90 | 90 | 0 | 0 |
| 24 | 95 | 80 | 95 | 50 |
| 25 | 0 | 0 | 0 | 0 |
| 26 | 10 | 0 | 0 | 0 |
| 29 | 20 | 0 | 0 | 0 |
| 30 | 95 | 90 | 75 | 35 |
| 31 | 98 | 95 | 60 | 45 |
| 32 | 99 | 95 | 85 | 30 |
| 33 | 100 | 100 | — | — |
| 34 | 25 | 15 | 15 | 15 |
| 35 | 40 | 30 | 10 | 0 |
| 36 | 10 | 0 | 10 | 0 |
| 37 | 0 | 0 | 0 | 5 |
| 40 | 40 | 40 | 10 | 10 |
| 41 | 90 | 85 | 0 | 0 |
| 44 | 75 | 20 | 5 | 35 |
| 46 | 100 | 100 | 100 | 99 |
| 47 | 80 | 80 | 55 | 30 |
| 48 | 0 | 0 | 0 | 0 |
| 49 | 100 | 95 | 100 | 100 |
| 50 | — | 100 | 100 | — |
| 52 | 20 | 0 | 10 | 5 |
| 53 | 70 | 60 | 30 | 10 |
| 54 | 90 | 75 | 85 | 25 |
| 55 | 100 | 100 | — | — |
| 56 | 65 | 90 | 5 | 0 |
| 57 | 90 | 80 | 60 | 40 |
| 58 | 80 | 80 | 0 | 0 |
| 59 | 98 | 97 | 79 | 58 |
| 60 | 100 | 100 | 97 | 95 |
| 61 | 10 | 10 | 0 | 0 |
| 62 | 100 | 100 | 99 | — |
| 63 | 95 | 90 | 85 | 45 |
| 64 | 94 | 88 | — | — |
| 65 | 78 | 64 | — | — |
| 66 | 100 | 100 | — | 99 |
| 67 | 87 | 94 | 97 | — |
| 68 | 73 | 66 | 96 | 67 |
| 69 | 100 | 100 | 98 | 98 |
| 70 | 100 | 100 | — | 100 |
| 71 | 20 | 10 | 0 | 0 |
| 73 | 50 | 34 | 10 | 0 |
| 74 | 60 | 40 | 0 | 0 |
| 75 | 100 | 91 | 99 | 100 |
| 76 | 100 | 100 | 100 | 100 |
| 77 | 100 | 68 | 80 | 57 |
| 78 | 100 | 97 | 100 | 100 |
| 79 | 100 | 100 | 100 | 100 |
| 80 | 100 | 100 | 65 | 51 |

TABLE III-continued
Wheat Leaf Rust Control by Foliar Application

| Example No. | % Control (without rain) 1 lb. | 0.25 lb. | % Control (with 1" of rain) 1 lb. | 0.25 lb. |
|---|---|---|---|---|
| 81 | 100 | 100 | 86 | 53 |
| 82 | 78 | 61 | 72 | 46 |
| 83 | 34 | 44 | 98 | 100 |
| 84 | 100 | 100 | 100 | 100 |
| 85 | 85 | 80 | 90 | 72 |
| 86 | 99 | 96 | 63 | 63 |
| 87 | 49 | 15 | 0 | 0 |
| 88 | 80 | 73 | 100 | 98 |
| 89 | 51 | 26 | 80 | 57 |
| 90 | 28 | 0 | 87 | 80 |
| 91 | 72 | 41 | 100 | 100 |
| 92 | 81 | 100 | 87 | 100 |
| 93 | 94 | 65 | 0 | 0 |
| 94 | 100 | 100 | 83 | 82 |
| 95 | 99 | 98 | 100 | 100 |
| 96 | 98 | 90 | 5 | 0 |
| 97 | 100 | 100 | 100 | 100 |
| 98 | 100 | 86 | 100 | 100 |
| 99 | 99 | 99 | 100 | 100 |
| 100 | 100 | 100 | 100 | 100 |
| 101 | 100 | 100 | 100 | 100 |
| 102 | 100 | 100 | 51 | 51 |
| 103 | 90 | 50 | 80 | 50 |
| 104 | 98 | 80 | 98 | 45 |
| 105 | 95 | 50 | 90 | 50 |
| 106 | 100 | 100 | 100 | 99 |
| 107 | 100 | 100 | 100 | 100 |
| 108 | 85 | 35 | 40 | 25 |
| 109 | 100 | 100 | 100 | 96 |
| 110 | 100 | 100 | 100 | 100 |
| 111 | 100 | 100 | 100 | 93 |
| 112 | 100 | 100 | 97 | 98 |
| 113 | 100 | 100 | 100 | 98 |
| 114 | 100 | 100 | 100 | 100 |
| 115 | 100 | 99 | 95 | 90 |
| 116 | 100 | 100 | 99 | 95 |
| 117 | 100 | 100 | 99 | 95 |
| 118 | 100 | 100 | 100 | 100 |
| 119 | 100 | 100 | 100 | 100 |
| 120 | 100 | 100 | 98 | 98 |
| 121 | 98 | 90 | 100 | 100 |
| 122 | 100 | 100 | 100 | 100 |
| 123 | 100 | 98 | 98 | 90 |
| 124 | 100 | 100 | 100 | 100 |
| 125 | 60 | 50 | 30 | 20 |
| 126 | 96 | 93 | 96 | 83 |
| 127 | 100 | 99 | 95 | 60 |
| 128 | 100 | 100 | 90 | 84 |
| 129 | 100 | 100 | 99 | 100 |
| 130 | 100 | 97 | — | — |

Other tests in which the spray residue was allowed to age for several days before being rained upon demonstrated excellent persistency.

The compounds of this invention which have exhibited excellent systemic activity in the control of cereal rusts are of the structure

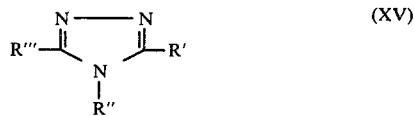

(XV)

wherein R' is hydrogen of the group —SA wherein A is hydrogen, cyano-substituted lower alkyl, lower alkoxy substituted lower alkyl, the group —CH(OH)CCl$_3$, —CH$_2$C(O)NR$^5$R$^6$ wherein R$^5$ and R$^6$ are hydrogen or lower alkyl, benzyl, methoxybenzyl, the group —C(X)NR$^5$R$^6$ wherein X is O or S and R$^5$ and R$^6$ are hydrogen or lower alkyl, methoxybenzoyl, furoyl, 2,4-dinitrophenyl and salt-forming metals; R" is alkyl or 3 to 6 carbon atoms exclusive of the tert-butyl group, lower alkoxy lower alkyl and benzyl; and R''' is hydrogen or the —COOB group wherein B is hydrogen, lower alkyl or a metal, ammonium, amine or quaternary ammonium salt-forming group.

The preferred compounds are those in which R" is a n-butyl group, e.g. 4-n-butyl-1,2,4-triazole, 3-mercapto-4-n-butyl-1,2,4-triazole and 3-mercapto-4-n-butyl-5-carboxy-1,2,4-triazole.

As one test for systemic activity the compounds were evaluated by a root-uptake method. In the root-uptake test one of the active compounds of this invention, contained in a suitable formulation, was incorporated into the soil by either spraying it into a rotating drum of soil, or by drenching the soil. The dosage of active ingredient in the soil ranged from about 50.0 to about 2.5 parts per million (pmm). Seeds of a susceptible wheat variety were planted in the treated soil and allowed to germinate and grow to a height of about 4 inches. The plants were then inoculated with a spore suspension of *Puccinia recondita*. The plants sprayed with spores of the rust fungus were then held at 70° F. in a moist chamber about 16 hours to permit infection. The lesions were allowed to develop about one week and were then counted in comparison to untreated plants and the percent disease control calculated. Table IV gives the results. Dashes indicate no data.

TABLE IV
Systemic Activity by Root-Uptake

| Example No. | R' | R" | R''' | % Systemic Wheat Leaf Rust Control ppm in Soil 20 | 10 | 5 | 25 |
|---|---|---|---|---|---|---|---|
| 1 | H | C$_3$H$_7$ | H | | — | 100 | 99 |
| 3 | H | n-C$_4$H$_9$ | H | | 100 | 100 | 100 |
| 4 | H | i-C$_4$H$_9$ | H | 100 | | | |
| 8 | H | i-C$_5$H$_{11}$ | H | 100 | | | |
| 9 | H | C$_6$H$_{13}$ | H | | — | 92 | 77 |
| 46 | H | CH$_3$OCH$_2$CH$_2$CH$_2$ | H | | — | 99 | 96 |
| 49 | H | C$_6$H$_5$CH$_2$ | H | | 99 | 98 | 96 |
| 57 | H | 3,4-Cl$_2$C$_6$H$_3$ | H | | 68 | — | 54 |
| 63 | H | 5-chloro-2-pyridyl | H | 95 | | | |
| 75 | SH | C$_3$H$_7$ | H | | 84 | 82 | 40 |
| 76 | SH | C$_4$H$_9$ | H | | 100 | 97 | 83 |
| 78 | —SH | C$_5$H$_{11}$ | H | | 97 | 97 | 97 |
| 79 | SH | C$_6$H$_{13}$ | H | | 54 | 0 | 0 |
| 84 | —SH | C$_6$H$_5$CH$_2$ | H | | 64 | 34 | 0 |
| 94 | —SH | C$_4$H$_9$ | COOH | | 100 | 99 | 95 |
| 85 | —SH | C$_4$H$_9$ | COONH(CH$_2$CH$_2$OH)$_3$ | | 100 | 99 | 98 |

TABLE IV-continued

Systemic Activity by Root-Uptake

| Example No. | R' | R'' | R''' | % Systemic Wheat Leaf Rust Control ppm in Soil | | |
|---|---|---|---|---|---|---|
| | | | | 20 | 10 | 5 |
| | | | | | | 25 |
| 97 | —SH | C4H9 | COOC2H5 | 100 | 95 | 93 |
| 98 | —SNa | C4H9 | COOC2H5 | 99 | 97 | 85 |
| 99 | —SC(O)NHCH3 | C4H9 | COOH | 100 | 99 | 96 |
| 100 | —SC(O)NHCH3 | C4H9 | COONH(CH2CH2OH)3 | 99 | 99 | 89 |
| 101 | —SC(S)N(CH3)2 | C4H9 | COOH | 100 | 96 | 88 |
| 106 | (2-(2-cyanoethyl)-4-n-butyl-1,2,4-triazoline-3-thione) | | | 92 | 86 | 82 |
| 107 | —SCH2CH2OC2H5 | C4H9 | H | 89 | 85 | 52 |
| 110 | —SCH(OH)CCl3 | C4H9 | H | 100 | 100 | 98 |
| 111 | —SCH2C(O)NH2 | C4H9 | H | 92 | 91 | 76 |
| 112 | —SCH2C6H4OCH3—4 | C4H9 | H | 72 | 71 | 64 |
| 113 | —SC6H3(NO2)2—2,4 | C4H9 | H | 100 | 94 | 67 |
| 114 | —SC(O)NHCH3 | C4H9 | H | 100 | 100 | 96 |
| 121 | —SC(O)C6H4OCH3—4 | C4H9 | H | 100 | 100 | 98 |
| 124 | —S—furoyl | C4H9 | H | 99 | 99 | 94 |
| 125 | —SCH2COC6H4OCH3—4 | C4H9 | H | 44 | 68 | 55 |

Another type of systemic test was conducted in which pots of approximately 5 inch high wheat plants were sprayed with varying concentrations of the test compound. Thirty-six hours later they were sprayed six minutes in a rain machine which amounted to about one inch of normal rainfall. The plants were then placed in a greenhouse for 7 days and then inoculated with a spore suspension of wheat leaf rust, *Puccinia recondita*. About 7 days later lesion counts were made on ten leaves representing the sprayed leaves and new growth from each replicate and compared with similar pots of wheat plants which were untreated with a chemical and the percent disease control determined. Disease control on the new growth is a measure of systemic activity. The commercial product known by the trademarked name Plantvax, which is 2,3-dihydro-5-carboxanilido-6-methyl-1,4-oxathiin-4,4-dioxide, was used as a standard. Table V gives the results.

TABLE V

Foliar Systemic Activity on Leaf Rust

| | % Rust Control | | | | | |
|---|---|---|---|---|---|---|
| | Sprayed Leaf | | | New Growth | | |
| Treatment Example No. | ½ | 1/6 | 1/12 | ½ | 1/6 | 1/12 |
| | (lb./100 gal.) | | | (lb./100 gal.) | | |
| 3 | 99 | 99 | 97 | 100 | 98 | 85 |
| 49 | 99 | 76 | 42 | 87 | 54 | 46 |
| 76 | 97 | 88 | 80 | 90 | 77 | 75 |
| 78 | 98 | 96 | 91 | 92 | 79 | 57 |
| 79 | 96 | 88 | 85 | 65 | 48 | 38 |
| 84 | 78 | 63 | 54 | 54 | 34 | 36 |
| 94 | 99 | 91 | 71 | 86 | 73 | 61 |
| 95 | 90 | 78 | 46 | 90 | 75 | 63 |
| 97 | 86 | 73 | 81 | 54 | 75 | 67 |
| 99 | 69 | 74 | 81 | 82 | 69 | 56 |
| 100 | 79 | 79 | 57 | 79 | 63 | 54 |
| 107 | 73 | 27 | 25 | 61 | 23 | 17 |
| 111 | 88 | 51 | 49 | 88 | 59 | 38 |
| 113 | 98 | 93 | 81 | 81 | 69 | 57 |
| 114 | 96 | 83 | 68 | 98 | 79 | 67 |
| 121 | 95 | 81 | 91 | 92 | 79 | 77 |
| 126 | 13 | 0 | 0 | 42 | 27 | 0 |
| Plantvax | 49 | 37 | 3 | 38 | 32 | — |

A field test was conducted in which 3-mercapto-4-n-butyl-1,2,4-triazole (the compound of Example 76), Plantvax and maneb (manganese ethylenebisdithiocarbamate) were evaluated for the control of leaf rust on winter wheat planted in September. Applications of the chemicals were made the following April when the wheat was 16–24 inches tall and in the boot stage. The volume of spray was 40 gallons per acre. Forty-six days after application lesion counts were made of 200 leaves per plot for four replications and compared with check (untreated) plots. This gives a measure of systemic control. Table VI gives the results.

TABLE VI

| | Systemic Field Test | |
|---|---|---|
| Treatment | lbs./acre | No. of lesions/800 leaves |
| Example 76 | 2 | 89 |
| | 1 | 239 |
| | 0.5 | 453 |
| Plantvax | 2 | 690 |
| | 1 | 1017 |
| | 0.5 | 1113 |
| Untreated | | 1109 |

A field test was conducted in which the compound of Example 76, the compound of Example 94, and Plantvax were evaluated for the control of leaf rust on spring wheat planted on May first. Forty one days after planting spray applications of the chemicals were made in a dosage series. Thirty-six days after treatment the disease control was evaluated by determining the percent leaves infected. Table VII gives the results.

TABLE VII

| | Systemic Field Test | |
|---|---|---|
| Treatment | lbs./acre | % Leaves infected |
| Example 76 | 0.5 | 23 |
| | 1 | 10 |
| | 2 | 4 |
| Example 94 | 0.5 | 35 |
| | 1 | 17 |
| | 2 | 7 |
| Plantvax | 0.5 | 79 |
| | 1 | 78 |
| | 2 | 75 |

Representative compounds of this invention have given good control of various fungal organisms. For example, compounds of the type

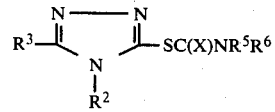 (XVI)

wherein $R^2$ is lower alkyl, $R^3$ is hydrogen and carboxy and its triethanol amine salts, $R^5$ and $R^6$ are hydrogen or lower alkyl, and X is O or S have given 80% or better kills of *Phytophthora infestans* at 1200 ppm. Compounds of Formula XIII wherein $R^{10}$ is alkyl or alkyl substituted with hydroxy, alkoxy or aryloxy, e.g. Examples 10, 18, 24, 25 and 47, have given good control of *Phytophthora infestans* by foliar application at 1200 ppm or by root uptake from treated soil containing 20 ppm. Example 13, 4-n-dodecyl-1,2,4-triazole, gave 95–100% control of rice blast, *Piricularia oryzae*, by foliar application at 1200 ppm. Example 112, 3-(4-methoxybenzylmercapto)-4-butyl-1,2,4-triazole, gave 50–85% control of *Botrytis cinerea* on broad bean at 1200 ppm. When beets were grown in a soil containing 200 ppm of Example 121, 3-(4-methoxy-benzoylmercapto)-4-butyl-1,2,4-triazole, an excellent control of *Pythium ultimum* was obtained.

The compounds of this invention may be utilized as the sole biocidal agents, alone or in admixture, or they may be employed in conjunction with other fungicides or with insecticides, miticides, bird repellents and comparable pesticides.

Fungicides which may be combined with the 1,2,4-triazoles of this invention include dithiocarbamates and derivates such as ferric dimethyldithiocarbamate (ferbam), zinc dimethyldithiocarbamate (ziram), manganese ethylenebisdithiocarbamate (maneb) and its coordination product with zinc ion, zinc ethylenebisdithiocarbamate (zineb), tetramethylthiuram disulfide (thiram) and 3,4-dimethyl-1,3,5-2H-tetrahydrothiadiazine-2-thione; nitrophenol derivatives such as dinitro-(1-methylheptyl)phenyl crotonate (dinocap), 2-sec-butyl-4,6-dinitrophenyl, 3,3-dimethylacrylate (binapacryl) and 2-sec-butyl-4,6-dinitrophenyl isopropyl carbonate, heterocyclic structures such as N-trichloromethylthiotetrahydro-phthalimide (captan), N-trichloromethylthiophthalimide (folpet), 2-heptadecyl-2-imidazoline (glyodin), 2,4-dichloro-6-(o-chloroanilino)-s-triazine, diethyl phthalimidophosphorothioate, 5-amino-1-[bis(-dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-B]quinoxaline (tioquinox), 1-butylcarbamoyl)-2-benzimidazole carbamic acid methyl ester, 4-(2-chlorophenylhydrazono)-3-methyl-5-isoxazolene, pyridine-2-thiol-1-oxide, 8-hydroxyquinoline, 2,3-dihydro-5-carboxanilido-6-methyl-1,4-oxathiin-4,4-dioxide, and bis(p-chlorophenyl)-3-pyridinemethanol; and miscellaneous fungicides such as dodecylguanidine acetate (dodine), 3-[2-(3,5-dimethyl-2-oxycyclohexyl)-2-hydroxyethyl]glutarimide (cycloheximide), phenylmercuric acetate, N-ethylmercuri-1,2,3,6-tetrahydro-3,6-endomethano-3,4,5,6,7,7- hexachlorophthalimide, phenylmercuric monoethanolammonium lactate, 2,3-dichloro-1,4-naphthoquinone, 1,4-dichloro-2,4-dimethoxybenzene, p-dimethylaminobenzenediazo sodium sulfonate, 2-chloro-1-nitropropane, polychloronitrobenzenes such as pentachloronitrobenzene, methyl isothiocycanate, fungicidal antibiotics such as griseofulvin or kasugamycin, tetrafluorodichloroacetone, 1-phenylthiosemicarbazide, Bordeaux mixture, nickel-containing compounds and sulfur.

We claim:

1. A compound of the formula:

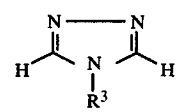

wherein $R^3$ is selected from the group consisting of n-pentyl, n-hexyl, n-octyl, n-decyl and n-dodecyl.

2. A compound according to claim 1 wherein $R^3$ is n-pentyl.

3. A compound according to claim 1 wherein $R^3$ is n-hexyl.

4. A compound according to claim 1 wherein $R^3$ is n-octyl.

5. A compound according to claim 1 wherein $R^3$ is n-decyl.

6. A compound according to claim 1 wherein $R^3$ is n-dodecyl.

* * * * *